(12) United States Patent
Orth et al.

(10) Patent No.: US 11,291,792 B2
(45) Date of Patent: Apr. 5, 2022

(54) PULMONARY VENTILATOR WITH CHANGEABLE FILTERS

(71) Applicant: BUNNELL INCORPORATED, Salt Lake City, UT (US)

(72) Inventors: Jeffrey L. Orth, Salt Lake City, UT (US); Ryan James Polcin, New Richmond, WI (US)

(73) Assignee: BUNNELL, INCORPORATED, Salt Lake City, UT (US)

(*) Notice: Subject to any disclaimer, the term of this patent is extended or adjusted under 35 U.S.C. 154(b) by 0 days.

(21) Appl. No.: 16/937,421

(22) Filed: Jul. 23, 2020

(65) Prior Publication Data

US 2021/0023325 A1 Jan. 28, 2021

Related U.S. Application Data

(60) Provisional application No. 62/878,170, filed on Jul. 24, 2019.

(51) Int. Cl.
*A61M 16/10* (2006.01)
*A61M 16/16* (2006.01)
(Continued)

(52) U.S. Cl.
CPC ........ *A61M 16/1065* (2014.02); *A61M 16/04* (2013.01); *A61M 16/0808* (2013.01);
(Continued)

(58) Field of Classification Search
CPC ............ A61M 16/105; A61M 16/1065; A61M 16/1055; A61M 16/04; A61M 16/08; A61M 16/10; A61M 16/0833; A61M 16/0808; A61M 16/12; A61M 16/16; A61M 16/208; A61M 16/106; A61M 16/107; A61M 16/0093; A61M 16/1045; B01D 46/00; B01D 46/0005; B01D 46/2411; B01D 27/00; B01D 35/00
(Continued)

(56) References Cited

U.S. PATENT DOCUMENTS 3,454,005 A 7/1969 Eubanks et al. ............... 128/186
3,494,113 A * 2/1970 Kinney .................. B01D 46/10
55/481

(Continued)

OTHER PUBLICATIONS

International Search Report and Written Opinion issued in PCT/US20/43327, dated Nov. 6, 2020, 10 pgs.
(Continued)

*Primary Examiner* — Valerie L Woodward
*Assistant Examiner* — Paige Kathleen Bugg
(74) *Attorney, Agent, or Firm* — Hayes Soloway P.C.

(57) ABSTRACT

In a pulmonary ventilation system, a filter arrangement useful as an input filter arrangement and an output filter arrangement is constructed to allow for changing or cleaning of the filter without interrupting or impacting the ventilation therapy and to limit the release of pathogens to the surrounding area or atmosphere. A preferred exhaust filter is constructed to function as a water trap and filter. Methods of operating the pulmonary ventilation system are also disclosed along with kits containing materials to construct an input or an output filtration structure.

19 Claims, 25 Drawing Sheets

(51) Int. Cl.
*A61M 16/04* (2006.01)
*A61M 16/08* (2006.01)
*A61M 16/12* (2006.01)
*A61M 16/20* (2006.01)

(52) U.S. Cl.
CPC ........ *A61M 16/0833* (2014.02); *A61M 16/12* (2013.01); *A61M 16/16* (2013.01); *A61M 16/208* (2013.01)

(58) Field of Classification Search
USPC .................................................... 128/203.26
See application file for complete search history.

(56) References Cited

U.S. PATENT DOCUMENTS

| | | | |
|---|---|---|---|
| 3,782,083 A | 1/1974 | Rosenberg | B01D 39/08 |
| 4,471,773 A | 9/1984 | Bunnell et al. | A61H 31/00 |
| 4,481,944 A | 11/1984 | Bunnell | A61B 7/00 |
| 4,681,099 A * | 7/1987 | Sato | A61M 16/024 |
| | | | 128/204.23 |
| 5,239,994 A | 8/1993 | Atkins | A61M 16/00 |
| 5,397,313 A | 3/1995 | Gross | A61M 5/315 |
| 5,546,935 A * | 8/1996 | Champeau | A61M 16/04 |
| | | | 128/204.23 |
| 5,752,506 A | 5/1998 | Richardson | A61H 31/00 |
| D441,449 S | 5/2001 | Gaskell | D24/162 |
| 6,279,574 B1 | 8/2001 | Richardson et al. | A61M 16/00 |
| 6,439,231 B1 | 8/2002 | Fukunaga et al. | A61M 16/00 |
| 6,619,287 B2 | 9/2003 | Blackhurst et al. | A62B 7/10 |
| 6,648,947 B2 * | 11/2003 | Paydar | B01D 46/0023 |
| | | | 55/385.1 |
| 6,886,561 B2 | 5/2005 | Bayron et al. | A62B 9/02 |
| 7,594,509 B2 * | 9/2009 | Burk | A61M 16/1045 |
| | | | 128/201.13 |
| 8,858,687 B2 * | 10/2014 | Jackson | B01D 46/22 |
| | | | 95/277 |
| 2009/0188217 A1 * | 7/2009 | Amann | A61M 16/107 |
| | | | 55/323 |
| 2010/0269828 A1 | 10/2010 | Orr et al. | A61M 16/00 |
| 2011/0126832 A1 * | 6/2011 | Winter | A61M 16/206 |
| | | | 128/204.21 |
| 2014/0261416 A1 * | 9/2014 | Arcilla | A61M 16/107 |
| | | | 128/203.14 |
| 2017/0095631 A1 | 4/2017 | Fukunaga | A61M 16/08 |
| 2017/0216549 A1 * | 8/2017 | Chang | A61M 16/16 |
| 2018/0207572 A1 * | 7/2018 | Grimes | B01D 39/12 |
| 2019/0255276 A1 * | 8/2019 | Van Schalkwyk | |
| | | | A61M 16/0066 |
| 2019/0344023 A1 * | 11/2019 | Boyes | A61M 16/106 |

OTHER PUBLICATIONS

Hylton, "Filtration of Breathing Gases", *Clinical Foundations*, 2011, item 0270, pp. 1-11.
Rumbaugh, et al., "Multidisciplinary System Critical Care Services, Inhaled Epoprostenol (Flolan®) Guidelines", Apr. 9, 2013 (Vanderbilt University Medical Center, Nashville, TN), 4 pgs.
Steen et al., "Automatic Non-Rebreathing Valve Circuits: Some Principles and Modifications", British Journal of Anesthesiology, 1963, 35, pp. 379-382.
LifePulse HFV User Manual, Model 204, Bunnell Incorporated, Inc., 2017, 110 pgs.
"BayWin Closed Circuit Valve" http://baywinvalve.com, accessed Dec. 21, 2020, 6 pgs.
"How to Use—Flusso by-Pass Adapter", https://flussobypass.com/how-to-use/, accessed Dec. 21, 2020, 3 pgs.

* cited by examiner

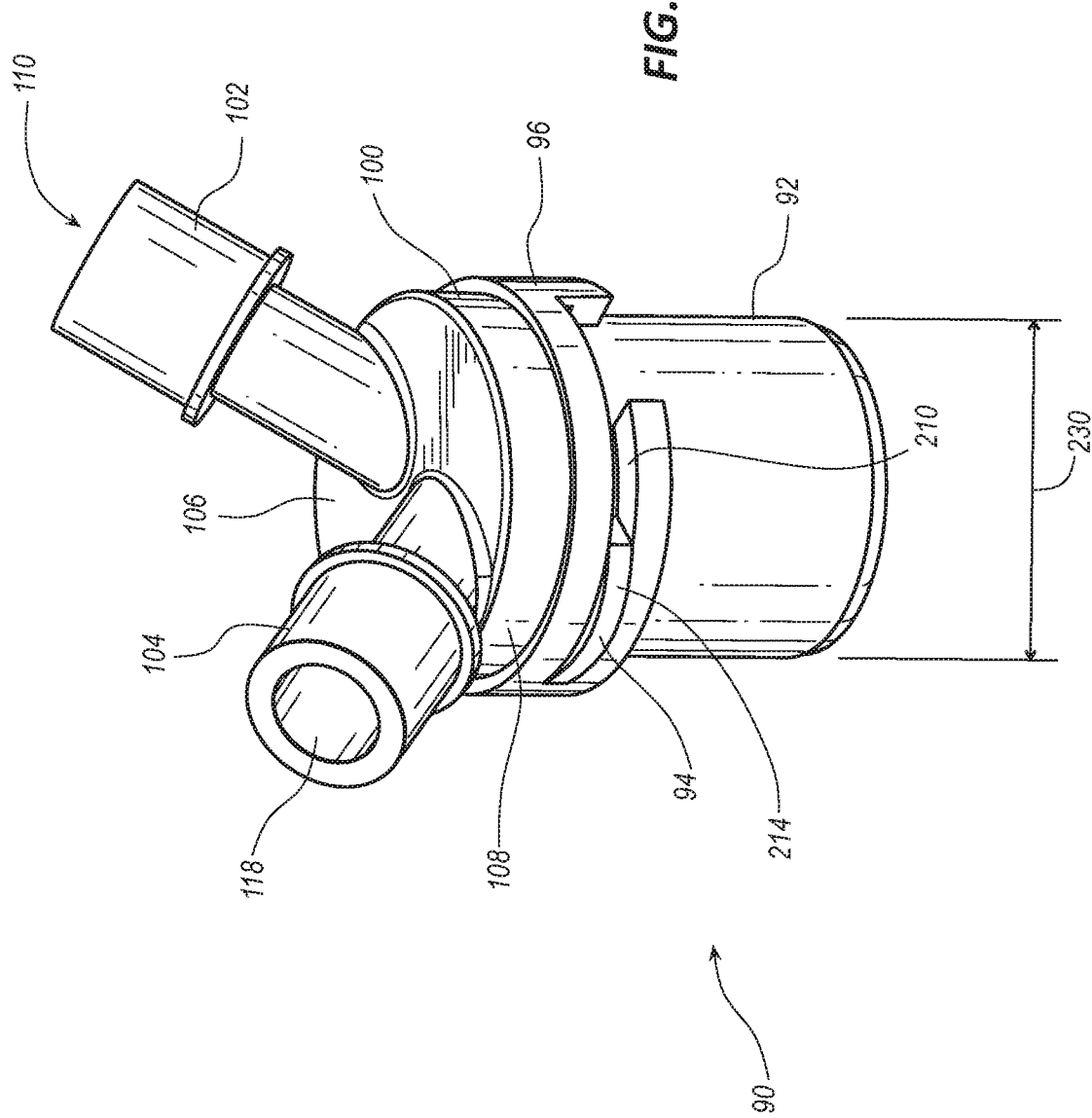

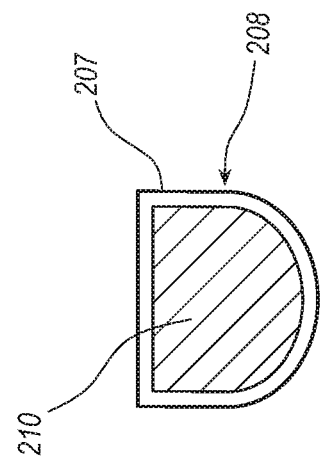
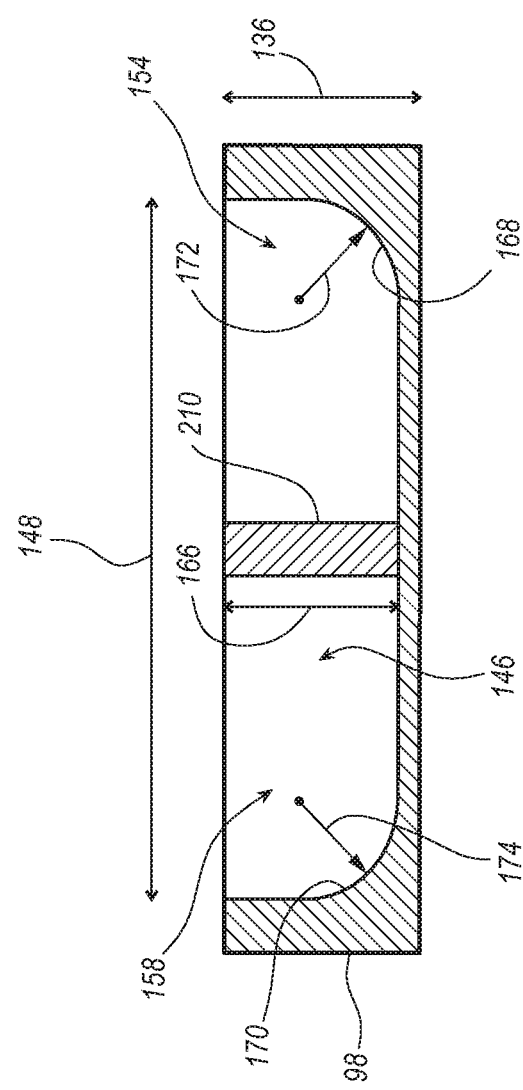

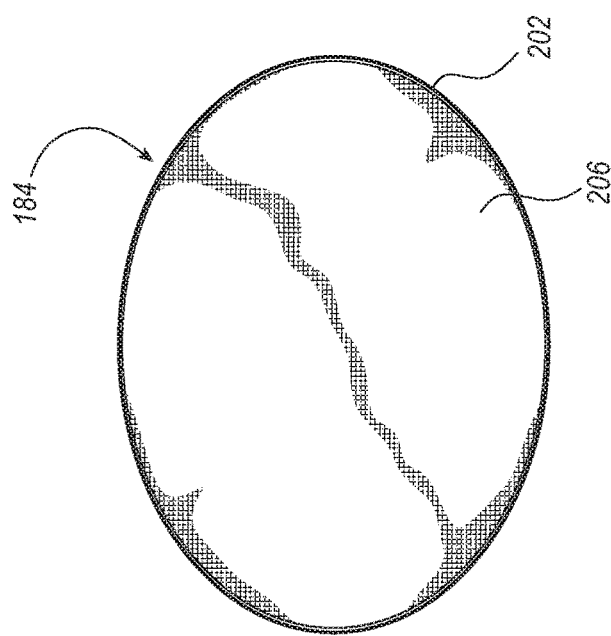
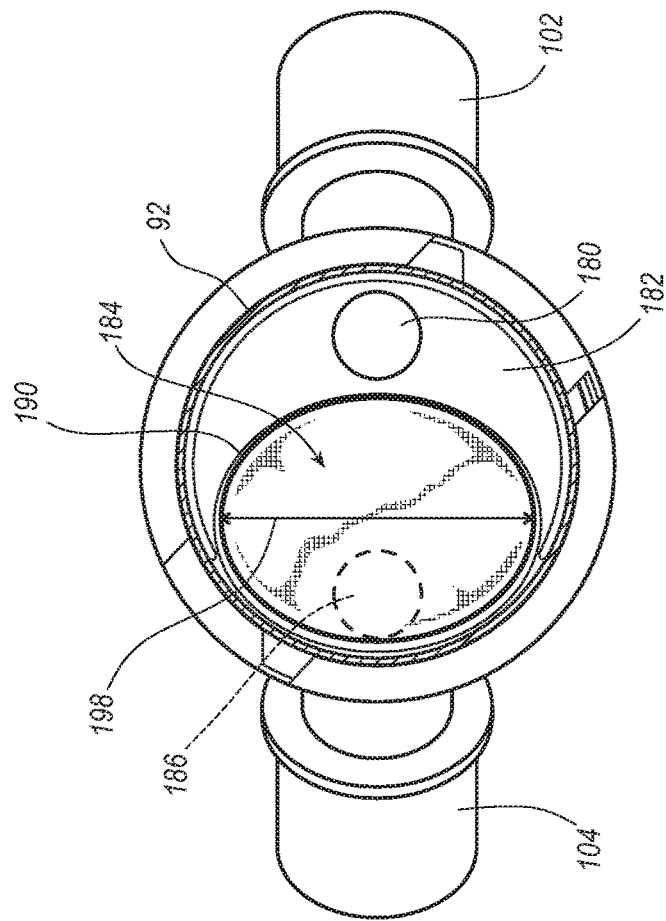
FIG. 6A
FIG. 6B

PULMONARY VENTILATOR WITH CHANGEABLE FILTERS

This application is a continuation-in-part of U.S. Provisional Patent Application Ser. No. 62/878,170 filed 24 Jul. 2019 the disclosure of which is incorporated by this reference as if fully set forth herein.

BACKGROUND OF THE INVENTION

1. The Field

A pulmonary ventilator system has a ventilator to supply blended gas to a patient through an inlet filter to form breathable gas for insertion into the trachea of a patient by a suitable input output structure. The breathable gas is used by and then exhausted by the patient along with moisture and pathogens from the patient to form an exhaust gas with pathogens which exhaust gas is directed to and through an exhaust filter in the exhaust limb. The inlet and exhaust filters have filter media which may be formed to be anti-bacterial and/or anti viral and are configured so that the filter itself or the filter media of each filter can be changed or cleaned without breaking the patient breathing circuit by, among other options, directing the breathable gas and exhaust gas through one of multiple paths each path having a separate filter or filter media. An HME filter may be included and similarly structured as the inlet and outlet filters. Further, the exhaust filter may be combined into and with a water trap which removes moisture from the exhaust gas.

2. The Relevant Technology

It is well known to supply a breathable gas to a patient as a medical therapy. A wide variety of pulmonary ventilators are known and commercially available. As an example, the PURITAN BENNETT® machines offered by Coviden Holding, Inc. of Mansfield, Mass. are known and supply breathable gas as or for respiratory or pulmonary therapy. Other pulmonary ventilation machines are known like the LIFE PULSE® machine offered by Bunnell, Inc. of Salt Lake City, Utah. As yet another example, a Servo n® offered by Maquet Critical Care AB Corporation of Solna, Sweden is a pulmonary ventilator machine known to supply breathable gas for small babies.

Typical pulmonary ventilation systems such as one illustrated in FIG. 1 (prior art) include a ventilator 10 that functions to supply blended gas 15 through input filtration 9 that has a supply filter 12 and an optional humidifier 14. The input filtration 9 receives blended gas 15 from ventilator 10 from an outlet 48 and through a first supply line 40. The blended gas 15 is filtered and then optionally humidified in the humidifier 14 and then supplied as breathable gas 11 to an input and output device such as endotracheal tube 16 that is inserted in the trachea of a patient 18. The breathable gas 11 may also be supplied directly into the trachea of the patient 18 through suitable tubing that functions as an input and output device and an opening formed in the trachea by suitable procedures (i.e., a tracheotomy). The filter 12 must be changed from time to time during operation which typically requires one to break the line 41 or otherwise break the supply of breathable gas 11 and thus interrupt the pulmonary therapy. Interrupting the pulmonary therapy even for a short time to effect filter change or replacement can be harmful to the patient.

Typically, the patient 18 is a human; but the patient may also be any animal that can be treated with breathable gas. The breathable gas 11 is taken in by the patient 18 through, and then exhausted through, a "Y" connector 7. The "Y" connector 7 has three legs. One leg is connected to receive breathable gas, another is connected to direct exhaust gas outwardly and a third is connected to an optional HME filter 17 which in turn is connected to the endotracheal tube 16. After the breathable gas 11 is inspirated into the lungs of the patient 18, it is thereafter exhausted from the patient 18 becoming exhaust gas 13 that includes pathogens which may have, for example, undesired bacteria or viruses obtained from the patient 18. The exhaust gas 13 with pathogens may also include water and water vapor from the patient 18. The exhaust gas 13 proceeds from the endotracheal tube 16 through an exhaust circuit 19 that includes the exhaust line 20 that communicates or directs the exhaust gas 13 to and through exhaust filtration structure 22. The exhaust filtration structure 22 includes an outlet filter 24 and may also include a water trap 26 to remove moisture from the exhaust gas 13.

The outlet filter 24 functions to remove or filter pathogens in the exhaust gas 13 to form filtered exhaust gas 25. The filtered exhaust gas 25 is then typically directed to or through an exhaust valve 28 associated with the ventilator 10. The filtered exhaust gas 25 can be vented to the atmosphere, but venting to the atmosphere is not generally recommended because ventilation processes can be interrupted.

The exhaust valve 28 along with a flow control device 30 and a blender 32 are controlled by the control 38 of the ventilator 10 to make sure that the inspiration gas flow is not interrupted. The control 38 has controls to allow an operator to choose or select desired respiration functions (e.g., pressure, respiration rate, gas blend). The ventilator 10 may also have a pressure transducer 33 to detect the pressure via sensor line 33A of the breathable gas 11 being delivered to the patient 18.

Air 34 and oxygen 36 are the typical gases supplied to the ventilator 10 and blended in the blender 32 to form the blended gas 15. The amount of air 34 and oxygen 36 supplied is controllable and may be adjusted by the flow control 30 associated with the ventilator so that the blended gas 15 and the breathable gas 11 may vary between essentially all air to air highly enriched with oxygen. The air 34 and the oxygen 36 may be available from central storage in hospitals and other medical facilities. Alternately, the air 34 may be drawn from the environment and compressed within the ventilator. While air and oxygen are the typical gases, other gases may be added or substituted.

Filtration of the inspiratory (breathable, inhaled) gas and expiratory (exhaust, exhaled) gas is of critical importance. *Clinical Foundations,* 2011, item 0270 (Filtration of Breathing Gases). Patients and caregivers may be exposed to pathogens in the air that come from many sources including other patients. Inspiratory filtration seeks to limit or inhibit the transfer of such pathogens to a patient from the surrounding environment; and expiratory filtration seeks to limit or inhibit the delivery of pathogens from a patient to the surrounding environment including the atmosphere around and near the patient as well as other patients and caregivers. Id. The HME filter when used (e.g., during transport of the patient) is understood to include an HME cartridge that functions to absorb heat and moisture from the exhaust gas provided by the patient and to release or transfer the heat and moisture to the breathable gas being inspirated by the patient. U.S. Pat. No. 7,594,509 (Burk).

For patients including especially those patients having a condition in which the exhaust gas has known infectious pathogens that need to be or should be filtered, exhaust filtration (e.g., exhaust filtration structure 22) is provided. Operators of the pulmonary ventilation system in use may monitor the operation of the exhaust filtration structure. In turn, when the exhaust filtration structure has a water trap (e.g., water trap 26), an operator monitors the water trap and typically empties it on a periodic basis as it starts to fill with water/moisture collected from the exhaust gas. The filter of the system in use (e.g., the filter 24 in the prior art system of FIG. 1) is also typically changed on a regular or periodic basis. The changing may vary from once every few hours to perhaps longer such as once every day or two.

An older water trap of the type comparable to those used in today's pulmonary therapy systems and useful as water trap 26 in FIG. 1 (prior art) is described in U.S. Pat. No. 3,454,005 (Eubanks, et al). Those skilled in the art will also understand that other commercial water traps are available today including, for example, one from Armstrong Medical Ltd of Coleraine, Northern Ireland. Medtronics also offers a Puritan-Bennett® water trap.

Typical filters in the exhaust filtration structure comparable to filter 24 in FIG. 1 (prior art) useful in respiratory or pulmonary systems can be seen in US Patent Design D441,449 (Gaskel), in U.S. Pat. No. 6,619,287 (Blackhurst, et. al.) and U.S. Pat. No. 3,782,083 (Rosenberg). It is understood that the CDC (Center for Disease Control) has announced the desired degree of filtration provided by the filter media in the filter and the recommended replacement intervals.

For pulmonary ventilation systems with a filter comparable to supply filter 12 to remove contaminants including pathogens from the blended gas 15, the filter 12 typically has an inlet connected by first supply line 40 to the outlet 48 of the ventilator to receive the blended gas 15 and then filter the blended gas 15 to remove the pathogens and other contaminants found in the air and gas supplied to form the blend. Filtration and optional humidification of the blended gas forms breathable gas 11. The breathable gas 11 is supplied through an outlet connected to a second supply line 41 that connects to the "Y" connector 7 which is then connected to the endotracheal tube 16. The humidifier 14, if included, may be interconnected between the filter 12 and the supply line 41. An HME filter 17 may also be connected between the "Y" connector 7 and the endotracheal tube particularly when a humidifier is not provided.

For patients whose lungs have been compromised or that have not yet developed, it is important to maintain a minimum intra-alveolar pressure to prevent collapse of the alveoli. This residual volume of gas in the lungs during exhalation, termed the Functional Residual Capacity, not only keeps the alveoli open but continues to exchange gases with the blood via diffusion during exhalation. To change the supply filter 12, the inspiration circuit is opened which temporarily interrupts ventilator therapy. Opening up the inspiration circuit or limb to change a filter and/or to change anything else interrupts that circuit and may lead to a loss of the Functional Residual Capacity, the collapse of the alveoli. Loss of the FRC can mean that steps must be taken to once again recruit these alveoli for breathing by application of opening pressures greater than the surface tension of the tissues. In all, the interruption of therapy can be harmful to the patient.

For pulmonary ventilation systems with an exhaust limb or circuit 19 having exhaust filtration structure such as exhaust filtration 22 arrangement to filter or remove pathogens from the exhaust gas, the filter such as outlet filter 24 in the exhaust filtration structure 22 typically has an inlet 20 connected to an exhaust line such as exhaust line 21. The exhaust filtration arrangement 22 also has an outlet 24B connected to an exhaust valve such as exhaust valve 28. To change the outlet filter 24 in the exhaust filtration arrangement 22, the exhaust circuit or limb 19 must be opened. That is, the exhaust filtration arrangement 22 (or the filter 24 itself inside the exhaust filtration arrangement) is disconnected at the inlet 20 and the outlet 24B so that the filter 24, can thereby be removed and discarded or removed and cleaned. In that process, the Functional Residual Capacity also may be lost or reduced impeding or compromising the respiratory therapy. At the same time, the exhaust gas 13 from the patient is unfiltered and discharged into the surrounding atmosphere with the pathogens until the filter is cleaned and replaced or a new filter is reconnected between and to the inlet 20 and outlet 24B.

Filtration is critical in cases where the patient has a disease or disorder that produces pathogens posing a serious health risk (e.g., ebola, measles, pneumonia, COVID 19) to the caregivers and to others in the vicinity. Such pathogens can even pose a risk to others throughout a treatment facility such as a hospital as the pathogens can be circulated by others moving nearby and maybe even be circulated by the building ventilation system.

As noted before, the United States Center for Disease Control ("CDC") has recommended replacement intervals for filters like supply filter 12 and outlet filter 24. In some cases, the filter like outlet filter 24 in the exhaust circuit 19 may become partially or fully blocked or clogged. In some cases that blocking or clogging can occur quickly particularly in the outlet filter so that the outlet filter 24 may need to be changed frequently (once every several hours) to once a day. Of course changing the outlet filter 24 at any interval means that the exhaust circuit 19 must be broken open with subsequent risk of reduced or complete loss of the Functional Residual Capacity (FRC) and exhaust gas 13 venting directly to the atmosphere or environment while the filter such as filter 24 is removed and replaced or cleaned. Similarly, changing the supply filter 12 as well as the HME filter 17 means that the lines supplying breathable air 11 must be broken interrupting the ventilation therapy and possibly resulting in exhaust gases from the patient including the pathogens therein exiting through the inspiration line. The more frequent the changing process is performed, the more pathogens are released to the surrounding atmosphere.

Systems with input filtration and exhaust filtration that prevents or limits, venting of unfiltered exhaust gas to the atmosphere are not known; and systems that include a bypass and multiple filter configurations are not known. Systems that combine the function of the water trap and the filter to further limit the release of unfiltered exhaust gas to the surrounding atmosphere are also not known.

SUMMARY

A pulmonary ventilator system and filter as disclosed is configured to provide uninterrupted ventilation therapy to a patient to avoid loss of FRC and prevent contamination of the environment with pathogens when changing filters. The pulmonary ventilation system disclosed is configured to transmit a breathable gas to a patient through an input and output structure like an endotracheal tube configured for introduction of said breathable gas into the trachea of the patient. The breathable gas is inspirated (i.e., breathes in or inhales) and then expirated (i.e., breathes out or exhales) by the patient all on a repetitive basis that correlates to respiration rate. The expired gas becomes an exhaust gas with pathogens obtained from the patient.

The ventilator of the pulmonary ventilator system as disclosed receives and mixes at least two different gases each from an external source to form the breathable gas that is delivered at a ventilator output. A supply line is connected to the ventilator output for receiving the breathable gas and delivering it through input filtration to input output structure for introducing the breathable gas into the trachea of the patient.

The pulmonary ventilator system disclosed also has an exhaust line which may also be referred to as an exhaust limb or exhaust circuit. The exhaust line has a first end connectable to the input and output structure for receiving the exhaust gas with the pathogens. The exhaust line has a second end spaced from the first end and connected to exhaust filtration structure that filters the pathogens from the exhaust gas to form filtered exhaust gas.

The exhaust filtration structure has an inlet connected to receive the exhaust gas and an outlet configured to supply the filtered exhaust gas from the exhaust filtration structure. A first conduit directs the exhaust gas from the inlet of the exhaust filtration structure (through an optional water trap) to a changeable outlet filter. A second conduit supplies the filtered exhaust gas from the changeable outlet filter to the outlet of the exhaust filtration structure. The changeable outlet filter has a first path directing the exhaust gas through a first filter and a second path directing the exhaust gas through a second filter.

The first filter is removable from the first path when the exhaust gas is directed to the second path. The first filter removes pathogens from the exhaust gas having pathogens from the patient to form first filtered exhaust gas. The second filter is also removable and removes pathogens from the exhaust gas with pathogens from the patient to form second filtered exhaust gas. It is configured to be removable from a second path when said exhaust gas is being directed through the first path to the outlet of the exhaust filtration structure.

The pulmonary ventilator system also has a discharge line having a first end connectable to the outlet of the exhaust filtration structure to receive the filtered exhaust gas without the pathogens from either the first path and the second path. In effect, a bypass is provided which is configured so that the ventilation of the patient is never interrupted to change the outlet filter. Also, the ventilator does not react to the stopping or loss of flow as the filter is changed and then compensate for the loss of flow by increasing the flow of breathable gas. Further, the fluids/moisture and pathogens from the patient are not introduced into the environment reducing the risk of exposing other patients, caregivers and any others in the surrounding environment.

In another configuration, the changeable outlet filter has a filter element holder or housing configured to hold a filter structure such as a cartridge. The filter element holder is configured to receive a first filter structure to be in a first path. When it is desired to change the first filter structure, the first filter structure is moved out of the first path preferably by the second filter structure which is then positioned in the filter element holder in the second path. In the first path and the second path, the change from the first filter structure and second filter structure is made so that in effect the change from the first path to the second path is essentially immediate so the stream of exhaust gas with pathogens continuing to be filtered without any practical interruption of the flow of the stream of exhaust gas with pathogens; and in turn the FRC is not affected. That is, the filter element is moved from a first position in the first path to a second position wherein the first filter element is removed from the first path to form said second path in which the second filter is in the stream of exhaust gas with pathogens.

In an alternate arrangement, the changeable filter of the pulmonary ventilator system has a first filter in a first path and a second filter in a second path. The changeable filter includes a valve connected to the first conduit and operable to direct the exhaust gas with said pathogens to either the first path or the second path. In turn, flow of exhaust gas with pathogens is directed from one filter in the first path to a second filter in the second path with virtually no interruption so the FRC is not affected. In turn, the first filter can be changed or cleaned with the flow of the exhaust gas in the second path; and the second filter can be changed or cleaned with the flow of the exhaust gas with the pathogens in the first path.

In an alternate arrangement, in a pulmonary ventilator system the exhaust gas includes a water trap to recover moisture in the exhaust gas. The water trap is connected in the first conduit to remove moisture from the exhaust gas before filtration.

Notably a filter is disclosed that is structured to filter the flow of a fluid or liquid without effectively interrupting the flow by directing the flow through a first filter in one path while a separate filter is cleaned or readied with the flow changed to a different or separate path through a new and separate filter. In one arrangement, the separate filter is urged into a filter element holder to urge out the first filter with the separate filter. The filter can be structured with filter media to filter pathogens as well as other contaminants. Alternately a valve can be included as part of the filter to direct the flow into one path through a first filter and into another or second path so that the flow can be directed from one to the other with virtually or effectively no interruption of flow. Such a filter can be used as the inlet filter and also as the HME filter in a pulmonary ventilation system.

Methods of changing a filter in the exhaust structure are also disclosed along with a kit to provide all that is needed to practice a disclosed method. The methods include steps to bypass a first filter in a first path that has been in use and preferably change to a new or second filter in second path while the used first filter is isolated, removed and replaced with a clean or new filter. The first filter is later put into service while the second filter is isolated, removed and replaced.

BRIEF DESCRIPTION OF THE DRAWINGS

To further clarify the advantages and features of the systems and structure herein disclosed, a more particular description is rendered with reference to the appended drawings. It should be understood that the drawings depict only typical embodiments and therefore are not to be considered limiting of the scope of the appended claims. More specifically:

FIG. 3 is a perspective of a combined filter and water trap for use in a pulmonary ventilation system;

FIG. 5A is a cross sectional view of a valve portion of the combined water trap and filter of FIG. 3;

FIG. 5B is a planar view of a filter for positioning in the valve portion of the combined filter and water trap of FIG. 5;

FIG. 6A is a top view of the filter holder of the combined filter and water trap of FIG. 3;

FIG. 6B is a top view of a filter element of the combined filter and water trap of FIG. 3;

DESCRIPTION

Figure 1:
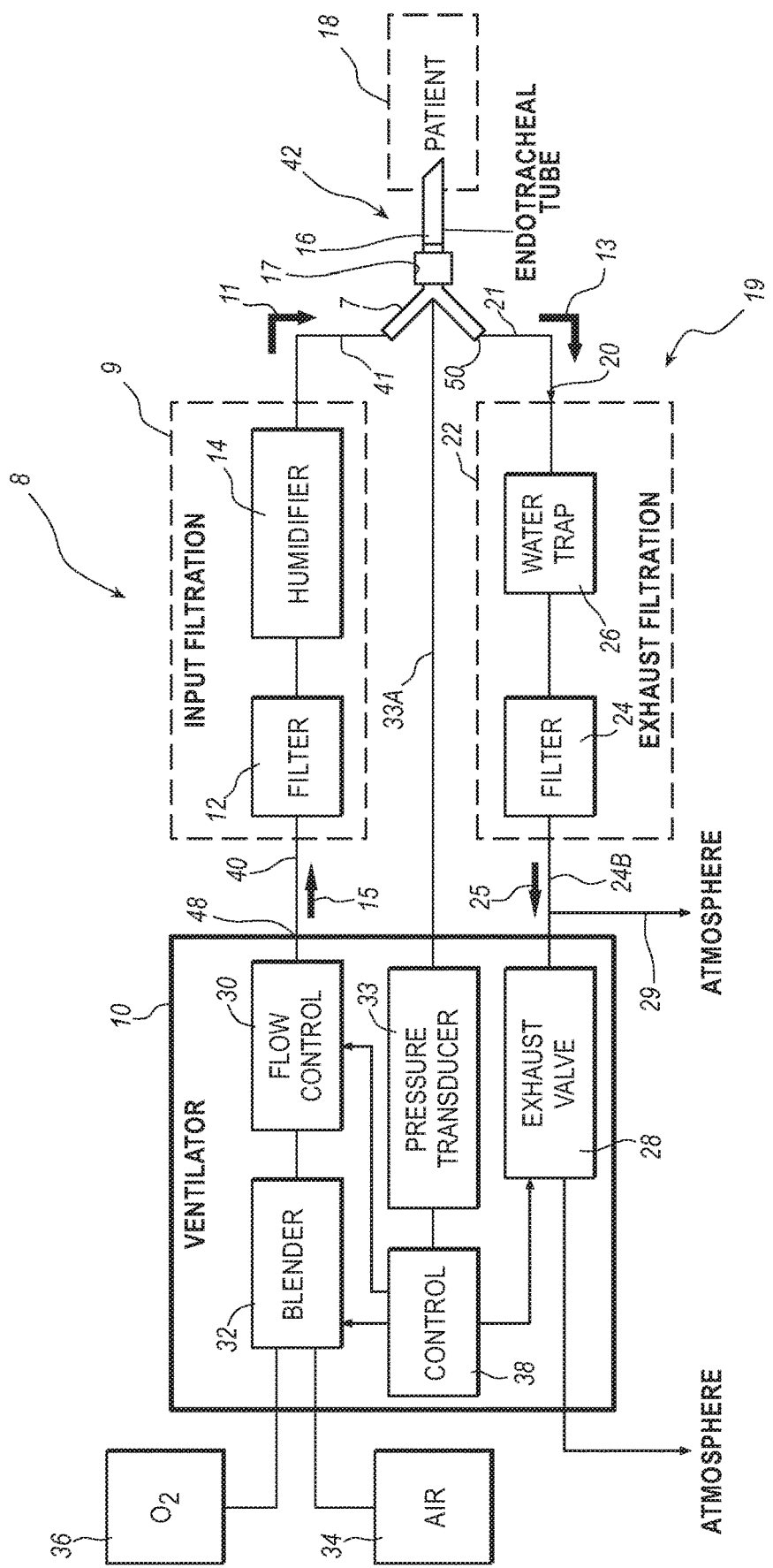
FIG. 1 is a block diagram of a prior art pulmonary ventilation system.

Hospitals, clinics, infirmaries, immediate or urgent care facilities and even medical offices of doctors and other medical practitioners may have patients visiting such places that carry pathogens exposing the treating medical practitioners and their related staffs (e.g., nurses, nurses aids, orderlies, nurse practitioners, administrators and other care givers) to those pathogens (e.g., a bacterium or bacteria as well as a virus such as COVID 19 or other microorganism that can cause disease). Efforts are being made to reduce the presence and/or spread of such pathogens in all locations using a wide variety of products, practices and procedures (e.g., widespread and frequent cleaning, hand washing, use of face masks, use of surgical gloves and gowns, use of disinfectants and the like).

To reduce the spread of pathogens in locations where patients receive pulmonary respiration or ventilation therapy, the exhaust of the pulmonary ventilation system (e.g., the exhaled breath from the infected patient) may be filtered to reduce the discharge of pathogens from the patient to the atmosphere as recommended by at least the CDC. That is, a filter may be placed in the exhaust limb or exhaust circuit of a pulmonary or respiratory therapy system; and then the filter is changed from time to time consistent with recommendations of agencies such as the CDC. Nevertheless, in known systems, the exhaust gas from the patient is vented directly into the environment of the patient at a location where the pulmonary respiration or ventilation therapy is being administered as the exhaust limb or exhaust circuit or line is opened up to remove and replace or clean the filter in the exhaust limb or exhaust circuit. When the exhaust circuit or limb is opened and the filter in the exhaust circuit or limb is removed, the exhaust gas vents directly to the nearby environment. The amount of exhaust gas that is released to the environment increases with the frequency of filter change (or cleaning) and the amount of time taken to complete the filter change or filter cleaning.

As stated hereinbefore, pulmonary ventilation systems are used to provide patients with pulmonary respiration or ventilation therapy in the form of breathable gas. The gas is typically a mixture of air and oxygen. The patient receives the breathable gas typically through an input and output structure such as an endotracheal tube that is inserted through the mouth into the trachea of the patient. The breathable gas may also be inserted using tubing directly inserted into the trachea following a tracheotomy procedure. The input and output structure may also be in the form of an oxygen mask that typically covers the nose and mouth. The breathable gas is inspirated as breathable gas and then expirated through the input and output structure such as the endotracheal tube as exhaust gas with pathogens and also with moisture from the patient entrained. That is, the pulmonary ventilation system has an exhaust limb or circuit to take the exhaust gas away from the patient through exhaust filtration structure to an exhaust valve (associated with a ventilator) which operates in accordance with control input from the ventilator control to maintain a virtually uninterrupted flow of breathable gas and avoid loss of FRC.

Also, as hereinbefore stated, the exhaust filtration limbs or circuits typically have a water trap to remove the moisture in the exhaust gas and a filter to remove pathogens from the gas. Water traps typically have a valve associated with them to facilitate removal. However, it is believed that cleaning or replacing the filter involves breaking the exhaust circuit and venting the exhaust gas with any pathogens therein to the atmosphere while the filter is being cleaned or a new or replacement filter or filter element installed. Systems and filter arrangements described hereinafter operate to minimize and preferably eliminate the release of exhaust gas with pathogens and the release of moisture to the atmosphere during the cleaning or changing of the filter and/or filter element in the exhaust limb or circuit.

The exhaust filtration structure disclosed herein may also include a filter and water trap combination. That is, a new valve structure includes the combination of a water trap feature and a filter structure along with a valve combined and used in a system to maintain ventilation while servicing the filter or water trap and to preclude or reduce the release of exhaust gas with pathogens to the environment surrounding the patient. Also disclosed is a kit the contents of which are to be used to form an exhaust filter structure for use with a pulmonary ventilation system which reduces the release of exhaust gas with pathogens to the environment.

Figure 2:
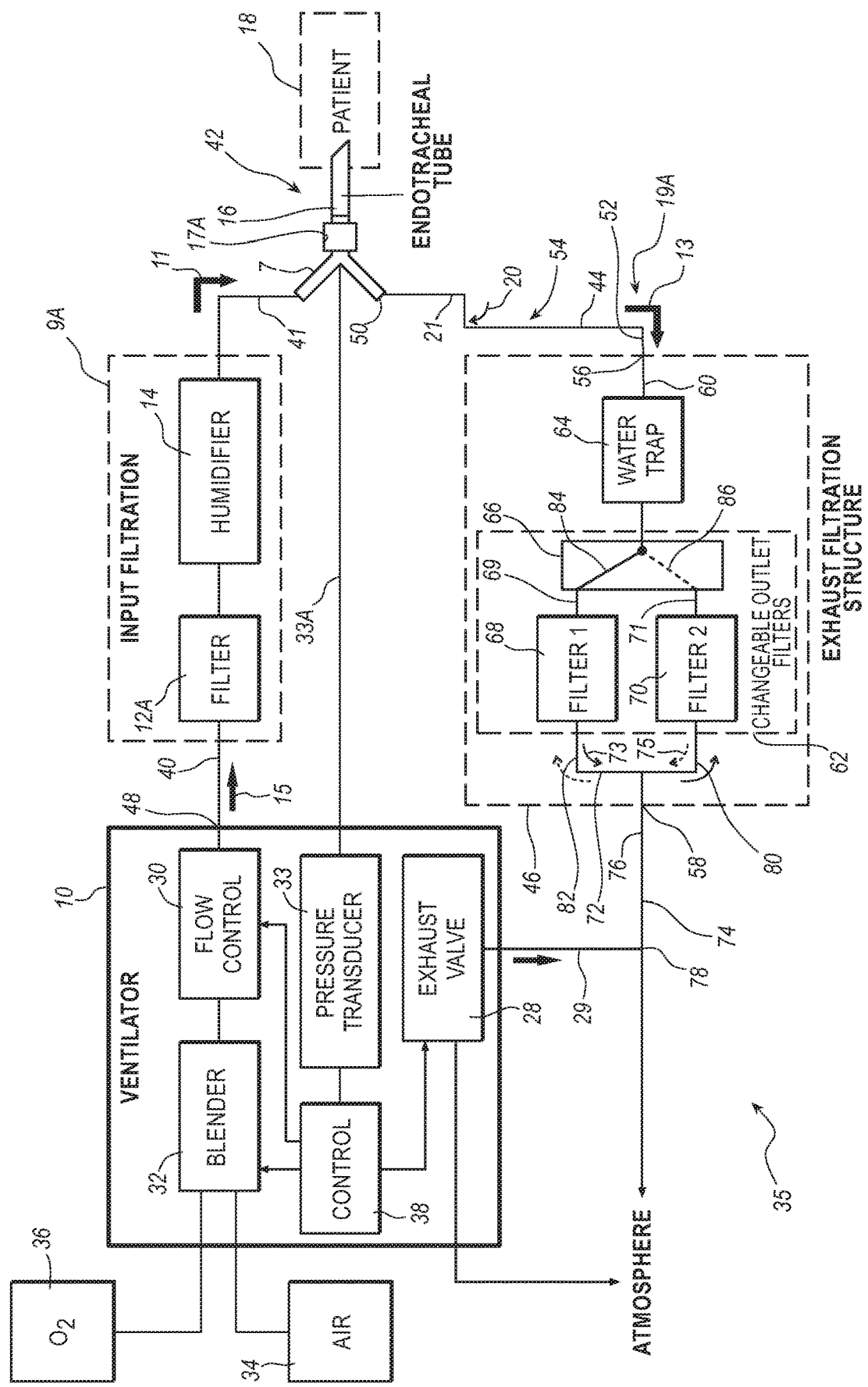
FIG. 2 is a block diagram depiction of a pulmonary ventilation system having exhaust filtration structure with changeable filters.

A new pulmonary ventilation system here disclosed in FIG. 2, uses some of the components of the pulmonary ventilation system of FIG. 1 However the pulmonary ventilation system of FIG. 1 has been modified to include an improved exhaust filtration structure 46 as well as improved input filtration 9A and an optional HME filter 17A. That is, the pulmonary ventilator system 35 herein illustrated in FIG. 2 receives two different gases which are blended to form blended gas 15. The two different gases are here seen as air 34 and oxygen 36. Other gases can be added or substituted. Various medicines can also be introduced into the blended gas 15 as desired. For example, Flolan® can be introduced into the inspiration line. See: Multidisciplinary System Critical Care Services, Inhaled Epoprostaol (Flolan®) Guidelines, Rumbaugh, et al, Apr. 9, 2013 (Vanderbilt University Medical Center, Nashville, Tenn.). The ventilator 10 is connected at a ventilator output 48 to first supply line 40 which directs or supplies blended gas 15 to the input of the input filtration structure 9A which includes filter 12A and humidifier 14. The second supply line 41 is connected to an input and output device such as the endotracheal tube 16 to supply breathable gas 11 which has been filtered by filter 12A and preferably humidified.

The new pulmonary ventilation system 35 of FIG. 2 has an exhaust limb or circuit 19A that includes exhaust lines 21 and 44 having a first end 50 connected to "Y" connector 7. The "Y" connector is also connected through another leg to and through HME filter 17A to the input and output device such as endotracheal tube 16. The exhaust line 21 receives the exhaust gas 13 and directs the exhaust gas 13 through the line 44 to the second end 52 of the exhaust line 44 with stretch 54 between the first end 50 and the second end 52. The second end 52 is connected to the inlet 56 of the exhaust filtration structure 46 which filters pathogens from the exhaust gas 13 and supplies filtered exhaust gas 73 and 75 at its outlet 58 as discussed hereinafter.

As seen in FIG. 2, a first conduit 60 is provided for the exhaust gas 13 to proceed from the inlet 56 to the changeable filter 62. In FIG. 2, an optional water trap 64 is positioned in the first conduit 60 to filter or remove moisture. The changeable filter 62 has a valve 66 to receive the exhaust gas 13 from the first conduit 60 directly or after being dewatered by the optional water trap 64. The exhaust gas 13 is directed to either a first filter 68 through a first leg 69 or a second filter 70 through a second leg 71. The exhaust gas 13 is then filtered by the first filter 68 to produce filtered exhaust gas 73 when the valve 66 is positioned in position 84 to direct the exhaust gas 13 through the first filter 68. Alternately, the exhaust gas 13 is filtered by the second filter 70 to produce filtered exhaust gas 75 when the valve 66 is positioned in position 86 to direct the exhaust gas 13 through the second filter 70. The second conduit 72 receives and conveys the filtered exhaust gas 73 to the second outlet 58. Similarly, a third conduit 80 conveys filtered exhaust gas 75 to the second outlet 58 when the valve 66 is in its second position 86. A discharge line 74 has a first end 76 connected to the second outlet 58 to direct the filtered exhaust gas 73 and 75 from the changeable filter 62 to its second end 78. The second end 78 may vent to the atmosphere or direct the filtered exhaust gas through an exhaust valve like exhaust valve 28 of ventilator 10.

In operation, it can be seen that the valve 66 is operable between a first position 84 (shown in solid line in FIG. 2) in which the exhaust gas 13 is directed toward the first filter 68. In that configuration, no exhaust gas 13 is proceeding to or into the second filter 70 which may be removed and replaced with a new second filter. Alternately, the second filter 70 may be removed, cleaned and replaced. With the valve 66 in the first position 84, filtered exhaust gas 73 from the first filter 68 may be released to the atmosphere through a third conduit 80 when the second filter 70 has been removed. When the new second filter or cleaned second filter is reinstalled, the filtered exhaust gas 73 all proceeds to the outlet 58.

With the valve 66 oriented in the second position (seen in dotted line in FIG. 2), the exhaust gas 13 is directed to the second filter 70. Because no exhaust gas 13 is being transmitted to the first filter 68, the first filter 68 may be removed and replaced with a new first filter. Alternately, the first filter 68 may be removed, cleaned and reinstalled. With the valve 66 in the second position, the filtered exhaust gas 75 from the second filter 70 is directed toward the discharge line 74 and may be released to the atmosphere through the third leg or first filter discharge line 82 when and while the first filter 68 is removed. With the valve 66 in either the first position 84 or the second position 86, only filtered exhaust gas 73 and 75 is released to the atmosphere with the pathogens in the exhaust gas 13 removed by either the first filter 68 or the second filter 70. And with the water trap 64 in place, the filtered exhaust gas 73 and 75 also has had moisture removed. Suitable check valves may be positioned between filter 68 and the discharge line 82 and between filter 70 and discharge line 80 to prevent back flow through a filter that has been removed for cleaning or replacement comparable to check valves discussed in connection with FIG. 2A. Suitable check valves include duck valves as well as valves having a thin vane deployed in the flow path. Suitable thin or flap valves may be available from Vernay Laboratories, Inc. of Atlanta, Ga. The check valve selected is of the type to optimally minimize pressure loss through the check valve.

Figure 2A:
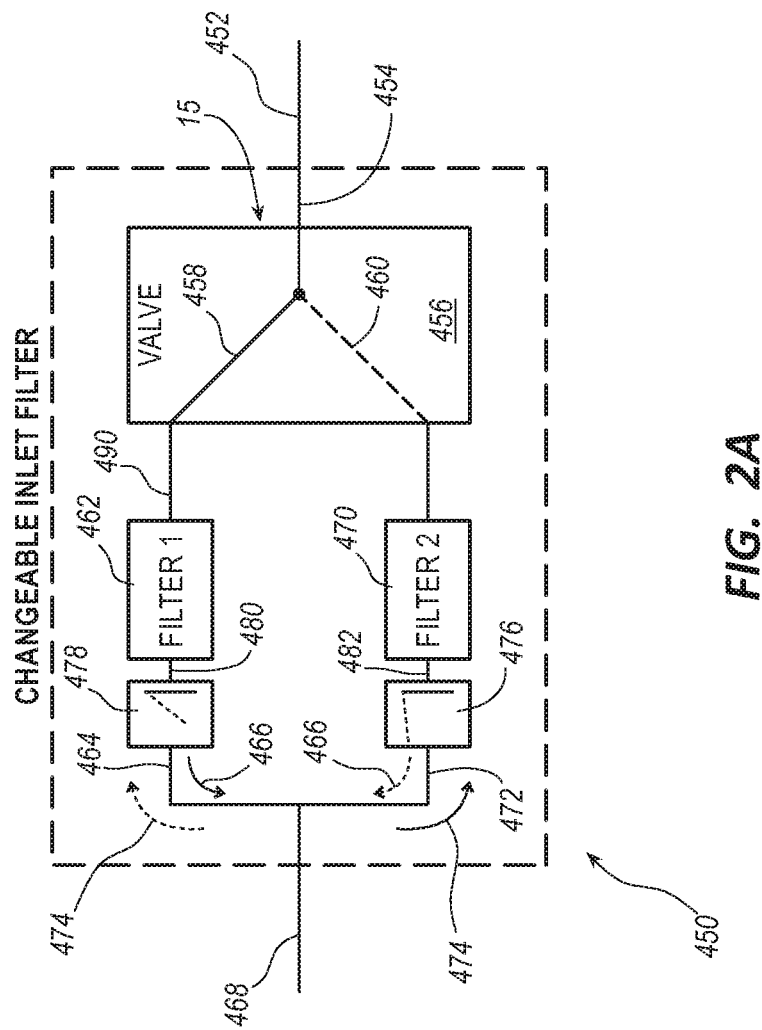
FIG. 2A is a block diagram depiction of an input filtration structure as disclosed herein for use in and with a pulmonary ventilation system.

As noted, the inlet ventilation system 35 disclosed also has input filtration 9A that includes changeable inlet filter 450 depicted in FIG. 2A. It receives the blended gas 15 from a ventilator like ventilator 10 through a first supply line 452 which is comparable to first supply line 40. The blended gas 15 then proceeds through a first input conduit 454 to valve 456 which has two positions, 458 and 460. In the first position 458 shown in solid, the blended gas 15 proceeds to filter 1 or a first filter 462 which is configured to remove pathogens (and any other foreign matter) and form first filtered gas 466. First filter 462 is also configured to be removable so that it can be replaced with a new filter to function as the first filter or Filter 1. That is, first filter 462 can be disconnected from first conduit 480 and second conduit 482. The fittings associated with the first conduit 480 and the first filter 462 are typically snug with the first conduit typically being female and frictionally inserted over a fixed male fitting associated with the filter 462.

After the blended gas 15 is filtered in the first filter 462 to remove contaminants including pathogens to produce first filtered gas 466, the first filtered gas 466 then proceeds to an outlet line 468 through a first check valve 478 discussed hereinafter and then a first filter leg 464. The outlet line 468 is connected to second supply line 41 for further connection to the input and output structure 42. A portion of the first filtered gas 466 may also proceed backward (shown in dotted line) through second filter leg 472 toward filter 2 or the second filter 470 when the valve 456 is in the first position 458 and the second filter 470 is removed for disposal and replacement with a new (clean) filter or removed for cleaning if it is of the type or kind that can be cleaned. With the second filter 470 removed, the first filtered gas 466 may exit to the atmosphere directly from the second filter leg 472 if there is no second check valve 476. If there is a second check valve 476 in the system, it will be configured to stop the flow of first filtered gas 466 therethrough so that all of the first filtered gas 466 proceeds to the outlet 468. The second check valve 476 is shown in the closed position in solid and an open position in dotted line.

When the valve 456 is in the second position 460 shown in dotted line, the blended gas 15 proceeds to the filter 2 or second filter 470 where the blended gas 15 is filtered to remove pathogens and any other unwanted material to form second filtered gas 474 which proceeds to the outlet 468 for further transmission. A portion of the second filtered gas 474 may also proceed as shown in dotted line through the first filter leg 464 when the first filter 462 is removed so it can be replaced or cleaned. Of course to stop the escape of second filtered gas 474 with the first filter 462 removed the first check valve 478 functions to close so that a portion of the second filtered gas 474 cannot escape there past and all will be directed to the outlet 468.

The use of first check valve 478 and second check valve 476 is preferable for the changeable inlet filter 450 as the flow of breathable gas 11 to the patient will not be interrupted or changed when an inlet filter such as first inlet filter 462 or the second inlet filter 470 is being changed. Thus the FRC remains unaffected. That is, the ventilation therapy is not then interrupted or modified as second filtered gas 474 does not vent or escape. Use of a system such as that illustrated in FIG. 2A allows ventilation therapy to remain stable or unchanged while each inlet filter 462 and 470 is being changed because the other remains in operation. In turn the ventilator like ventilator 10 also does not react to vary the breathable gas being supplied in an effort to maintain the breathable gas 11 as desired. The first filtered gas 466 and the second filtered gas 474 may also proceed through a humidifier like humidifier 14 to form breathable gas 11.

In operation, the changeable inlet filter 450 can operate through one filter like first filter 462 with the valve 456 in a first position 458 until first filter 462 becomes contaminated. When the valve 456 is in the first position 458, the second filter 470 can be removed and replaced with a new and clean filter or cleaned. The valve 456 may then be moved to the other or second position 460 directing the blended gas to the second filter 470 so that the first filter 462 can be removed and replaced with a new filter or cleaned. Inasmuch as the first filter 462 and the second filter 470 are of the same size and type as are the replacements, the supply of breathable gas 11 remains essentially unchanged and of suitable or desired quality.

Turning now to FIGS. 3-7, a combined water trap and filter 90 is depicted to function in the pulmonary ventilation system of FIG. 2 as the exhaust filtration structure 46. That is, the function of the water trap 64 and the function of the changeable filter 62 are combined into one to be the water trap and a filter.

Figure 7:
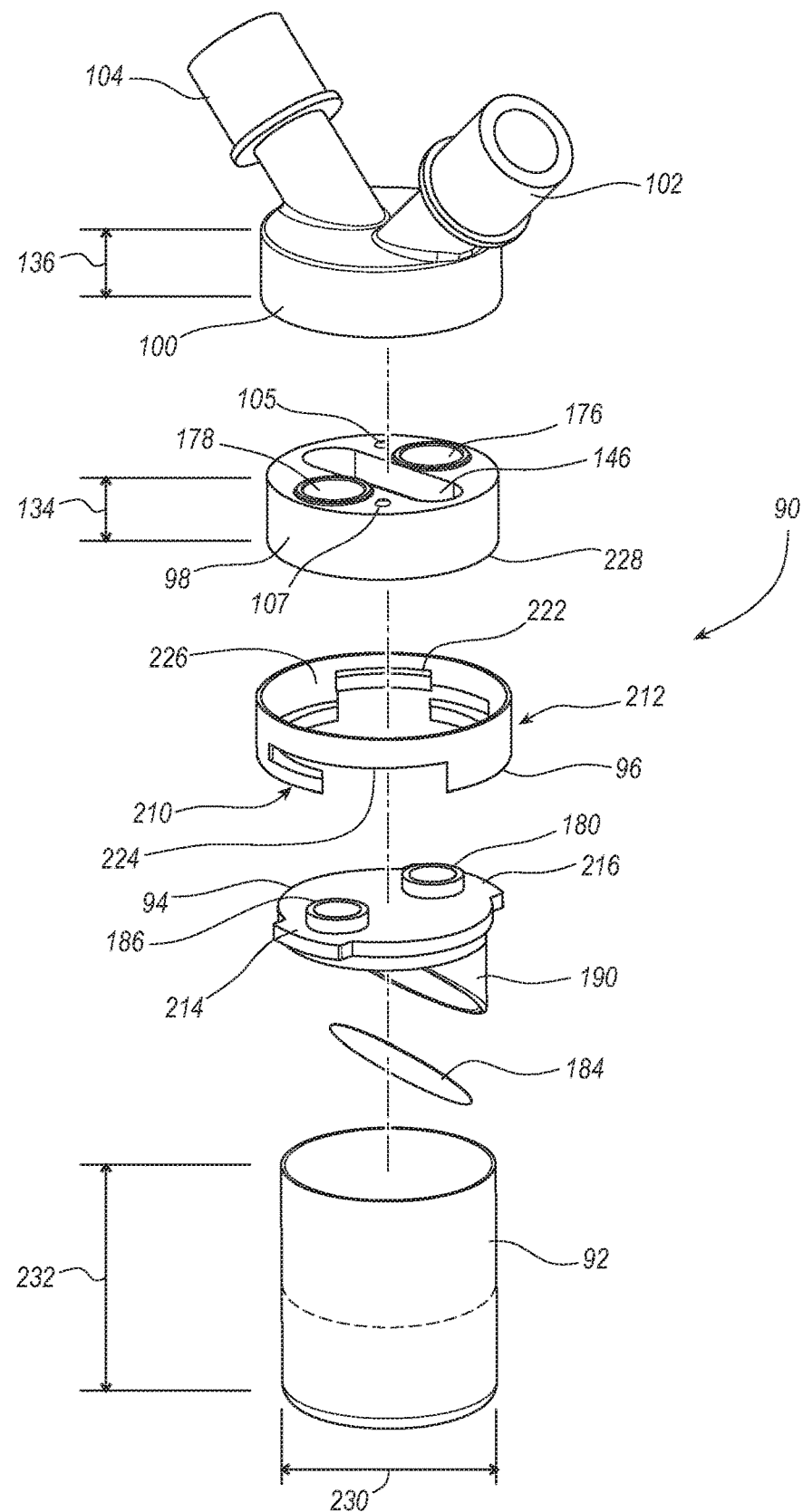
FIG. 7 is a fully exploded perspective of the combined filter and water trap of FIG. 3.

As depicted best in the exploded view of FIG. 7, the water trap and filter 90 has a receptacle or cup 92 secured to a filter holder 94. The receptacle or cup 92 has the filter holder 94 securely attached thereto. The attachment may be done by glue, plastic welding or by any other means to effect a water and air tight connection. In some configurations, it may be desired to provide for a threaded connection to provide access to and to allow for changing the filter as hereinafter discussed. But the preferred arrangement has a filter holder 94 glued to the receptacle or cup 92. The filter holder 94 has a tube 190 with a filter membrane 184 secured thereto. As a result, when the filter holder 94 is removed, the cup 92 and the filter membrane 184 are removed with it and may be disposed of and replaced with a new filter holder 94 and cup 92 with a new filter membrane 184.

The port 100 has an inlet 102 to receive exhaust gas 13 and direct it through the cup 92 and filter membrane 184 to the outlet 104 to supply filtered exhaust gas in a first configuration. In a second configuration, the exhaust gas 13 as received in the inlet 102 is directed straight to the outlet 104, all as discussed hereinafter. The port 100 has a top 106 and a side 108. As seen, the side 108 is circular in projection while the top 106 is essentially planar.

Figure 4:
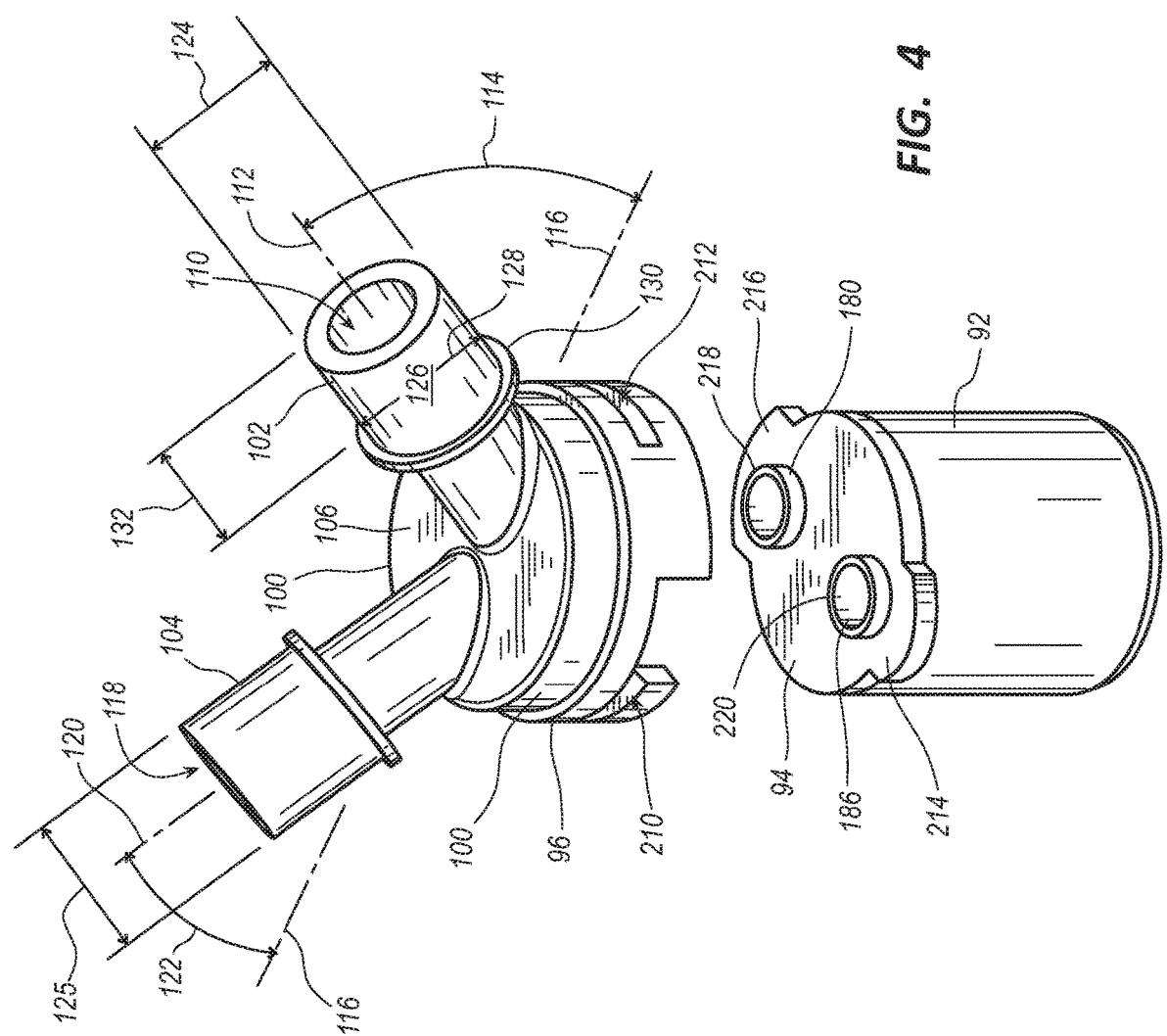
FIG. 4 is a partially exploded perspective of the combined filter and water trap of FIG. 3.

As best seen in FIG. 4, the inlet 102 has a channel 110 (that is shown to be tubular) with an axis 112 oriented at an angle 114 which may vary from a few degrees above the plane 116 of the top 106 to as much as 90 degrees. The angle 114 is preferably from about 30 degrees to about 60 degrees and most preferably about 45 degrees. Similarly, the outlet 104 has channel 118 (that is also shown to be tubular) with an axis 120 oriented at an angle 122 relative to the plane 116 of the top 100. The angle 122 also may vary from a few degrees (e.g., 5-10 degrees) above the plane 116 of the top to as much as 90 degrees. The angle 122 is preferably from about 30 degrees to about 60 degrees and most preferably about 45 degrees. In the most preferred configurations, the angle 114 and the angle 122 are the same.

It may also be noted that the inlet 102 has an outside diameter 124 and an inside diameter 126 both sized to receive typical flexible tubing used in pulmonary ventilation systems. Similarly, the outlet 104 has an outside diameter 125 and an inside diameter 164. Both the inlet 102 and the outlet 104 are configured to comply with International Standard ISO 5356-1 (4th Ed.: 2015). The typical flexible tubing is 22 millimeters (mm) in diameter for use with adult patients. The inside diameter of the inlet 102 is designed to mate with smaller, 15 mm diameter pediatric tubing sets. Suitable size adapters may also be used to accommodate tubing of different diameters.

The inlet 102 has a receiving portion 126 that may be tapered to have a larger outside diameter 128 abutting the collar 130 to allow the tubing to more easily be affixed to abut the collar 130 and effect a secure air tight connection. The receiving portion 126 also has a length 132 to facilitate the desired secure air tight connection. The inlet 102 is constructed as a conical inlet; and the outlet 104 is constructed to be a socket. Both are constructed in accordance with the ISO standard identified hereinbefore.

The valve 98 best seen in FIG. 7 is cylindrical in shape and sized to fit snugly but not entirely into the port 100. That is, the valve 98 has a thickness 134 slightly more than the thickness 136 of the port 100 to form a gap 144 to allow the port 100 to be rotatable relative to the valve 98.

Figure 5:
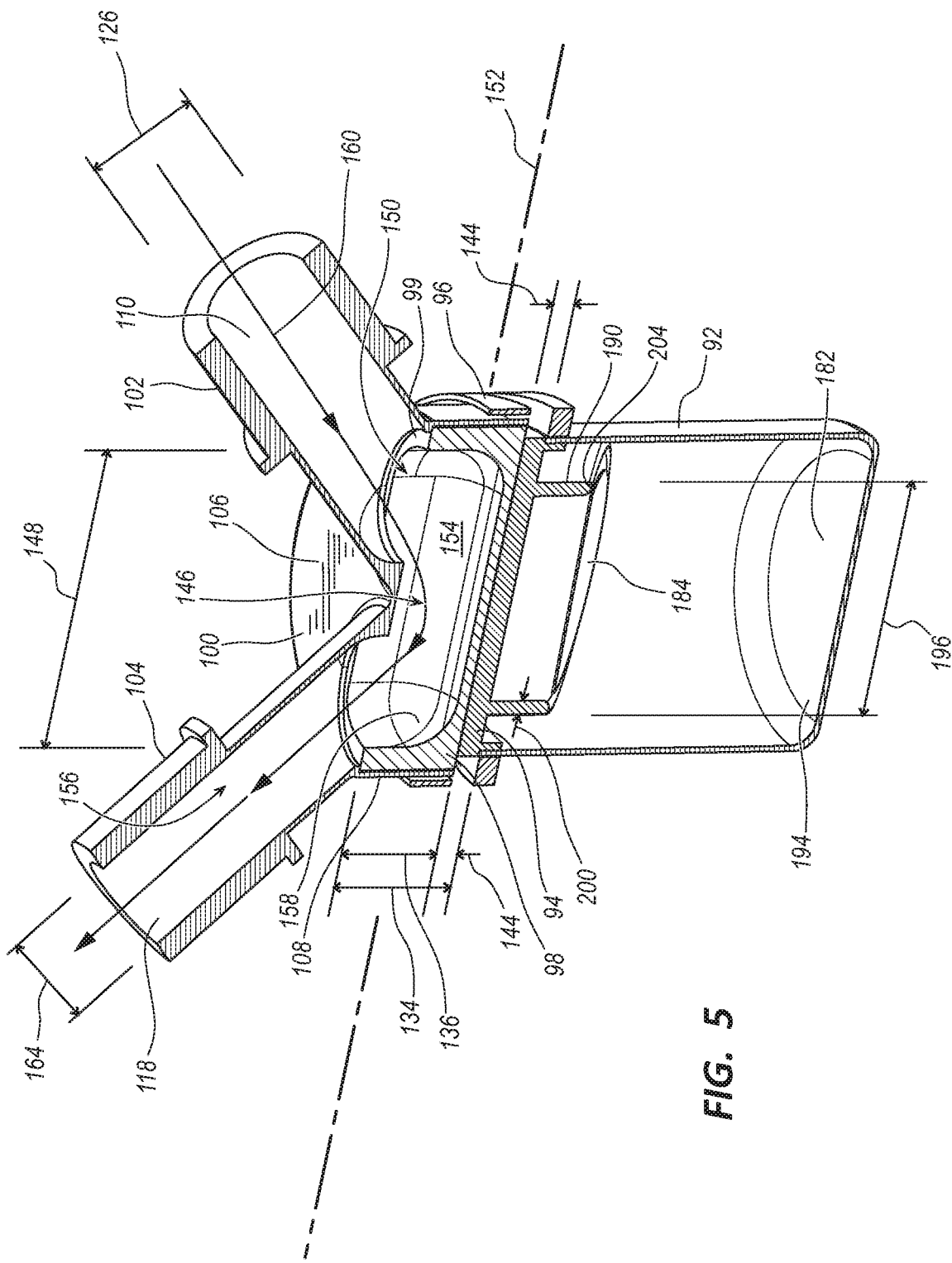
FIG. 5 is a cutaway cross sectional view of the combined filter and water trap of FIG. 3 in a bypass position.

The valve 98 has a slot 146 which is elongated having a length 148 extending along a center line 152 as better seen in FIGS. 5 and 5A to extend from or between the inlet 102 and outlet 104. That is, the inlet 102 has the channel 110 that extends to an opening 150 in the top 106 to register with one end 154 of the slot 146. The outlet 104 also has its channel 118 that extends to an opening 156 in the top 106 that registers with the other end 158 of the slot 146. As best seen in FIG. 5, in a first position or position A, the exhaust gas 13 from the input and output device 42 proceeds down the channel 110 of the inlet 102 of port 100 through the opening 150 and into the slot 146. The exhaust gas 13 then proceeds through the slot 146 to the opening 156 of the outlet and into the channel 118 of the outlet as indicated by flow path arrow 160. With the port 100 positioned as shown, the exhaust gas 13 proceeds from the inlet 102 to the outlet 104 so that the exhaust gas is unfiltered and proceeding directly to the exhaust valve 28 or to the atmosphere. The filter holder 94 and receptacle or cup 92 may be quickly and easily removed and replaced in a few seconds so that the amount of exhaust gas released is nominal. The pressure in the cup will vary from 0 to about 125 centimeters of water (cmH20) which is from about 0 to about 1.77 pounds per square inch with the actual pressure in the range of 10 to 80 cm $H_2O$ leading to a flow rate that can vary from about 2 to about 50 liters of exhaust gas 13 per minute. Alternately, a small section of filter material may be placed in the channel 146 to form a first path to filter the exhaust gas 13 coming in the inlet 102 so that no unfiltered gas is delivered at the outlet 104. Since the configuration with the exhaust gas 13 passing from the inlet 102 through the channel 146 directly to the outlet 104 would be used for short periods of time, it is expected that the filter material would last for an extended period of time (e.g., weeks) before it would need to be changed.

The channel 110 of the inlet 102 is shown to be circular in cross section having an inside diameter 126 and in turn an area comparable to the cross sectional area of the standard 1 inch supply hose that is the exhaust limb or exhaust circuit from the input and output device 42. The outlet 104 is also circular in cross section having an inside diameter 164 that is here selected to be the same as the inside diameter 126 of the inlet 102. In turn the cross sectional area of the inlet 102 is the same as the cross sectional area of the outlet 104. In some applications, the cross sectional area of the outlet 104 may be larger than the cross sectional area of the inlet 102 to avoid constricting the flow of the exhaust gas and creating a back pressure. The discharge may also have a functional larger cross sectional area so that the discharge does not restrict flow.

Referring back to FIGS. 5 and 5A, the slot 146 is semicircular in cross section between one end 154 and the other end 158. The diameter 166 of the channel or slot 146 is selected so that the area for the passage of the exhaust gas 13 from the one end 154 to the other end 158 is comparable to or slightly larger (e.g. 5% larger) than the area of the inlet channel 110 so that the slot 146 does not function as an orifice and create a construction to restrict the passage of the exhaust gas 13. As seen in FIG. 5A, a filter 208 is sized to fit into the slot or channel 146 to filter the exhaust gas when the valve is in the first position. The filter 208 is semicircular with a frame 207 and filter media 210 as seen in FIG. 5B that is selected to meet CDC standards. Further, the filter media 210 may be impregnated with anti viral and anti bacterial compounds.

As seen in FIG. 5A, it may also be noted that the slot 146 is rounded 168 at the one end and rounded 170 at the other end 158. The rounded ends 154 and 158 have a radius 172 and 174 that is comparable to and preferably the same as the radius 166 of the slot 146.

In operation, it can be seen in FIG. 5 that the port 100 is in a second position in which the inlet 102 and the outlet 104 are aligned. When the port 100 is in the second position, the exhaust gas 13 follows the flow path indicated by the arrow 160. The valve 98 is urged upward toward the top 106 of the port 100 to effect a frictional seal between the top 106 and the top surface 99 of the valve 98. In some instances, a sealing lubricant can be used to enhance the seal. Alternately a seal (not shown) made of a suitable seal material like TEFLON® material or a nylon type material may be placed between the top 106 and the top surface 99 of the valve 98 so that the port 100 may rotate relative to the valve 98 and still effect a seal so that the exhaust gas 13 proceeds as desired.

Figure 6:
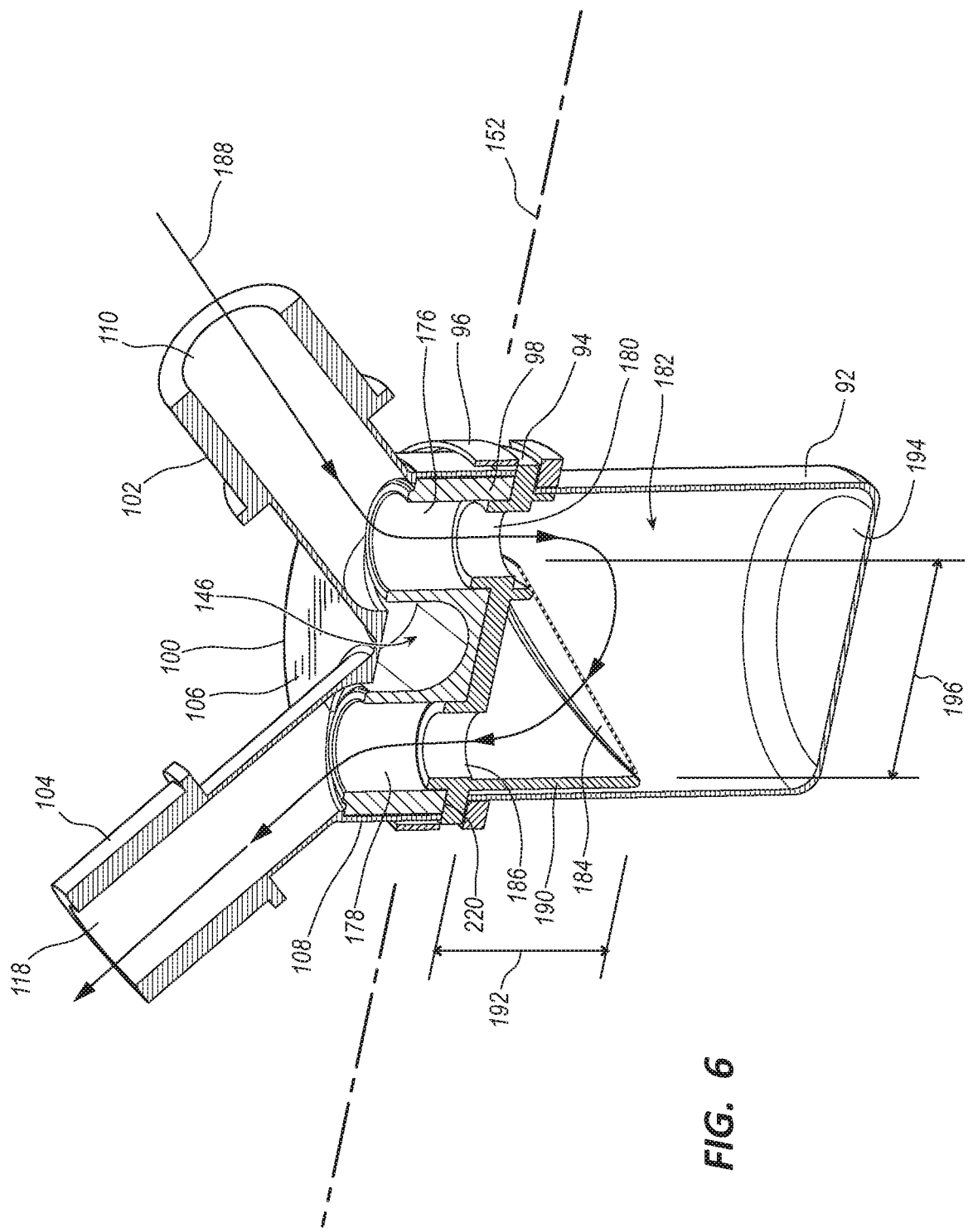
FIG. 6 is a cutaway cross sectional view of the combined filter and water trap of FIG. 3 in a filter position.

As stated, to use the filter and water trap 90, the port 100 may be rotated to a first position relative to the valve 98 to form a second path and align the inlet 102 and the outlet 104 to register with or mate with valve aperture 176 at the inlet 102 and valve aperture 178 at the outlet 104 as better seen in FIG. 6. When the port 100 is positioned relative to the valve 98 as seen in FIG. 6, the exhaust gas 13 is directed to flow through the channel 110 of the inlet 102 through the inlet valve aperture 176 and through the inlet aperture 180 of the filter holder 94 into the interior 182 of the receptacle or cup 92. The exhaust gas collects in the interior 182 and is then directed to and changes direction to pass through filter membrane 184 and then out through the outlet aperture 186 of the filter holder 94 and into the outlet aperture 178 and the channel 118 of the outlet 104. The flow path from the inlet 102 to the outlet 104 is shown in FIG. 6 by arrow or line 188.

In other words, the valve 98 can be rotated between a first or filtering position as seen in FIG. 6 and a bypass or non filtering position as seen in FIG. 5. To preclude accidental rotation or misalignment of the valve 98 relative to the port 100, the valve 98 is provided with two spring loaded balls 105 and 107 that register with corresponding detents (not illustrated) formed in the top 106 of the port 100. When a cup and filter holder 92 is attached, the ports on the filter holder 180 and 186 mate with the holes 176 and 178 of the valve 98. Rotating the cup and filter holder 92 to latch it to the full assembly then rotates the valve 98 to the flow-through position or second path. Rotating the cup to remove it rotates the valve to the bypass or first position or first path seen best in FIG. 5.

In FIG. 6, it can be seen that the filter holder 94 has a trunk 190 that is ovular in cross section as better seen in FIG. 6A. The trunk 190 extends into the interior 182 of the receptacle or cup 92 and has the filter membrane 184 secured thereto. The trunk 190 is truncated so that the filter membrane 184 is circular in projection having a diameter 196 that is the same as the diameter 198 of the trunk 190. The filter membrane 184 preferably has a rim 202 to register with the rim 204 of the trunk 190. That is, rim 204 of the trunk has a width 200 sized to mate with the rim 202. The rim 202 may extend beyond the rim 204 of the trunk and is preferably secured thereto by suitable glue or bonding material.

The trunk 190 has a height so that when the filter holder 94 is affixed to the receptacle or cup 92, the trunk extends from the filter holder 94 to the bottom 194 of the receptacle or the cup 92. The filter 184 has a membrane or filter material 206 having a porosity to filter out pathogens. The filter material 206 may also be impregnated with various substances to attack the pathogens. That is, the filter material is impregnated with anti bacterial and anti viral substances to enhance the filtration. The filter material 206 may also be pleated to increase the surface area of the filter to enhance filtration and reduce back pressure.

As also seen in FIGS. 5 and 6, the receptacle or cup 92 has an interior 182 that has a volume sufficient to allow moisture or other liquids to condense and collect therein. That is, the change of direction and the changes in pressure experienced by the exhaust gas 13 allows moisture to condense and collect in the volume of the interior 182 of the receptacle or cup 92.

As seen in FIGS. 3 and 4, the latching ring 96 has slots 210 and 212 to receive the tongues 214 and 216 of the filter holder 94. As seen the slots 210 and 212 as well as the tongues 214 and 216 are opposite each other and are sized so the tongues 214 and 216 register with the slots 210 and 212 and may slide in the slots 210 and 212 to effect a locking relationship. The surfaces of the slots 210 and 212 may be inclined so the slots 210 and 212 ramp or incline effect a frictional fit and in turn secure the filter holder 94 to the latching ring 96.

In FIG. 7, the latching ring 96 is shown with ledges 222 and 224 (shown in dotted line) on the interior surface 226. The bottom surface 228 of the valve is inserted into the latching ring 96 to abut the ledges 222 and 224 with the inlet aperture 180 of the filter holder 94 and the outlet aperture 186 of the filter holder 94 registering with the inlet valve aperture 176 and the outlet valve aperture 178 respectively as best seen in FIGS. 6 and 7. In some configurations, a ⅛ inch to ¼ inch thick spring like material (not shown) like neoprene may be placed on the ledges 222 and 224 to urge the valve 98 up toward the top 106 of the port 100. The latching ring 96 is bonded to the valve 98 by any suitable bonding material.

Referring again to FIG. 7, the receptacle or cup 92 is shown to be cylindrical in shape with a diameter 230 (FIG. 3) that may range from about 1.5 inches to about 2.5 inches with a height 232 from about 1.5 inches to about 2.5 inches with an interior 182 having a volume sufficient to trap moisture and liquids as the exhaust gas passes therethrough. The truncated trunk 190 allows for a circular opening with the filter membrane 184 positioned thereover. The filter membrane 184 seen in FIG. 6B is spaced above the bottom 194 a distance of less than ⅛ of an inch to allow liquid to gather without impacting on the area of the filter membrane 184 available to filter the exhaust gas. If the moisture or liquid has a level in the receptacle or cup 92 so that a portion of the area of the filter membrane 184 affixed to the trunk 190 is covered with liquid, the combined filter holder 186 and receptacle or cup 92 with the filter membrane 184 should be removed and should be placed in a suitable disposal device. That is, the valve 98 and port 100 may be removed from the locking ring 96 so that the filter holder 94 may be rotated out of the slots 210 and 212 for disposal. A new or replacement combination of filter holder 94 with receptacle or cup 92 attached thereto (with a new filter membrane 184) may then be assembled to the latching ring 96 for further assembly with the valve 98 and port 100.

In FIGS. 5 and 6, it can be seen that the port 100 when assembled over the valve 98 is sized to fit snuggly and rotatably inside the locking ring 96. As assembled, the port 100 may be rotated between a first position or position A in which the exhaust gas passes through as shown by the flow arrow 160 and a second position or position B in which the exhaust gas passes through the receptacle or cup 92 and through the filter membrane 184 as seen by the flow arrow 188.

Figure 8:
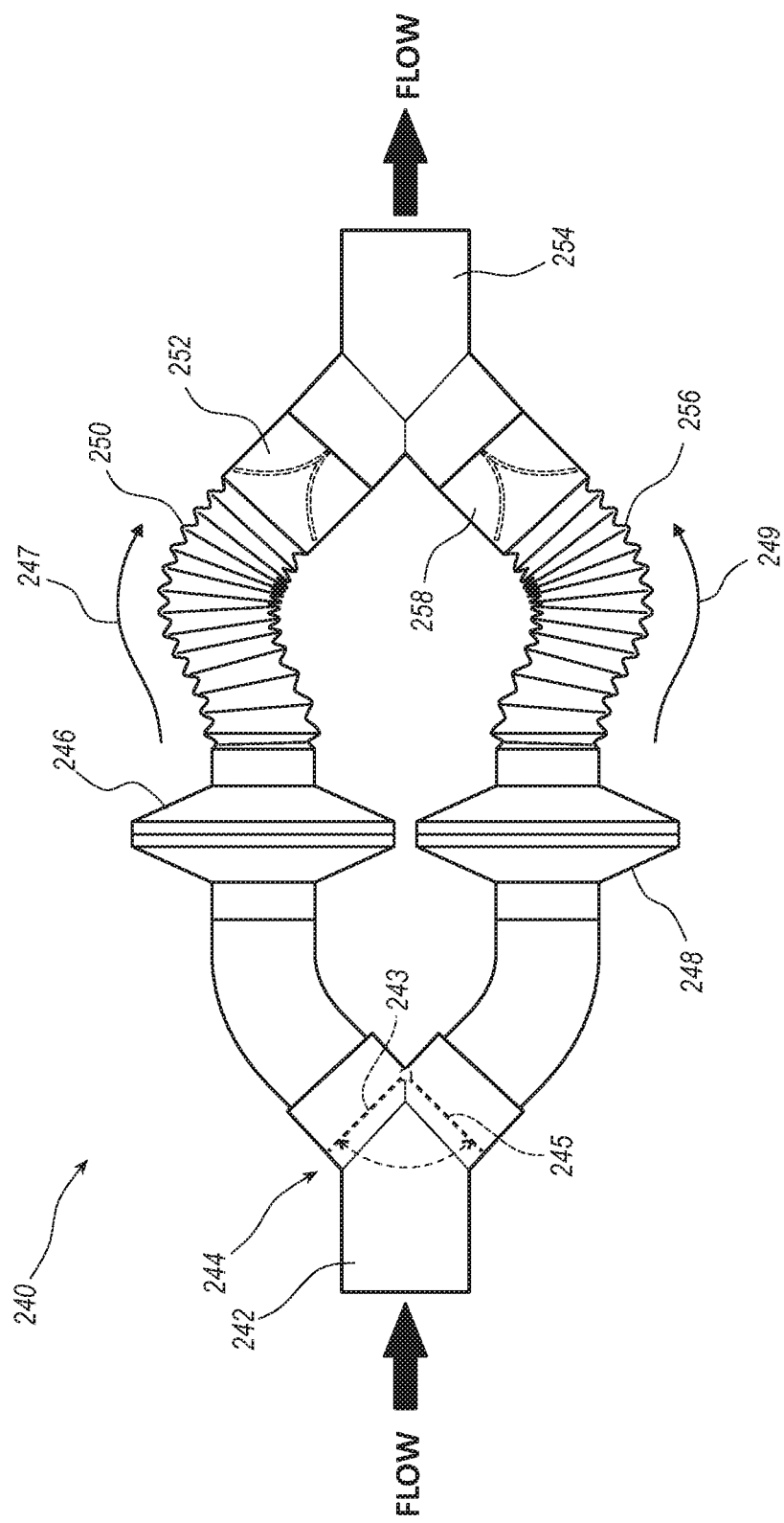
FIG. 8 is a depiction of a dual path changeable filter for use in a pulmonary ventilation system.

Turning now to FIG. 8, changeable filter 240 is depicted which may be used as the changeable outlet filter 62 (FIG. 2) in an exhaust filtration structure such as exhaust filtration structure 46. The changeable filter 240 as depicted may also be used as the changeable inlet filter 450 seen in FIG. 2A.

The changeable filter 240 of FIG. 8 has a first conduit 242 to receive exhaust gas 13 or blended gas 15 and direct it or supply it to a vane valve 244. The vane valve 244 is operable between a first position 243 (shown in solid) and a second position 245 (shown in dotted line). In the first position 243, the exhaust gas 13 or blended gas 15 is supplied or directed to a first disposable filter 246. When the vane valve 244 is in its second position 245, the exhaust gas 13 or blended gas 15 is supplied or directed to a second disposable filter 248. The exhaust gas 13 or blended gas 15 from the first disposable filter 246 is filtered to remove at least pathogens to form first filtered gas 247 which is supplied through a first exit conduit 250 and a first check valve 252 to an outlet 254. With the vane valve 244 reoriented to the second position 245 (shown in dotted line), the exhaust gas 13 or blended gas is directed to the second disposable filter 248 which functions to remove pathogens from the patient in the exhaust gas 13 to form second filtered gas 249 that is directed to and through a second exit conduit 256 and a second check valve 258 to the outlet 254. As can be seen, filtered exhaust gas 247 and 249 cannot pass or vent back through either check valve 252 and 258 so that all first filtered gas 247 and second filtered gas 249 must proceed to and through the outlet 254. The outlet 254 supplies the first filtered gas 247 and second filtered gas 249 to the atmosphere or to an exhaust valve comparable to exhaust valve 28 (FIG. 1) in a ventilation system so that sensors associated with the ventilator such as ventilator 10 can determine pressures and volumes of the first filtered gas 247 and second filtered gas 249.

Figure 10:
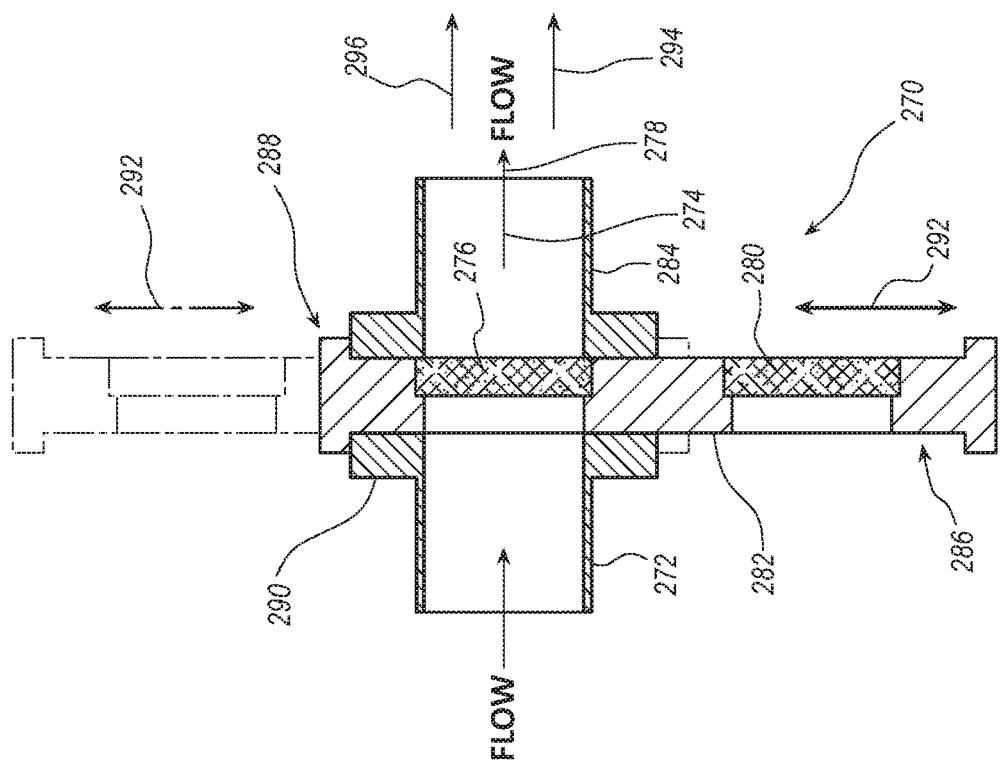
FIG. 10 is a cross sectional depiction of the single path dual filter system of FIG. 9.
Figure 9:
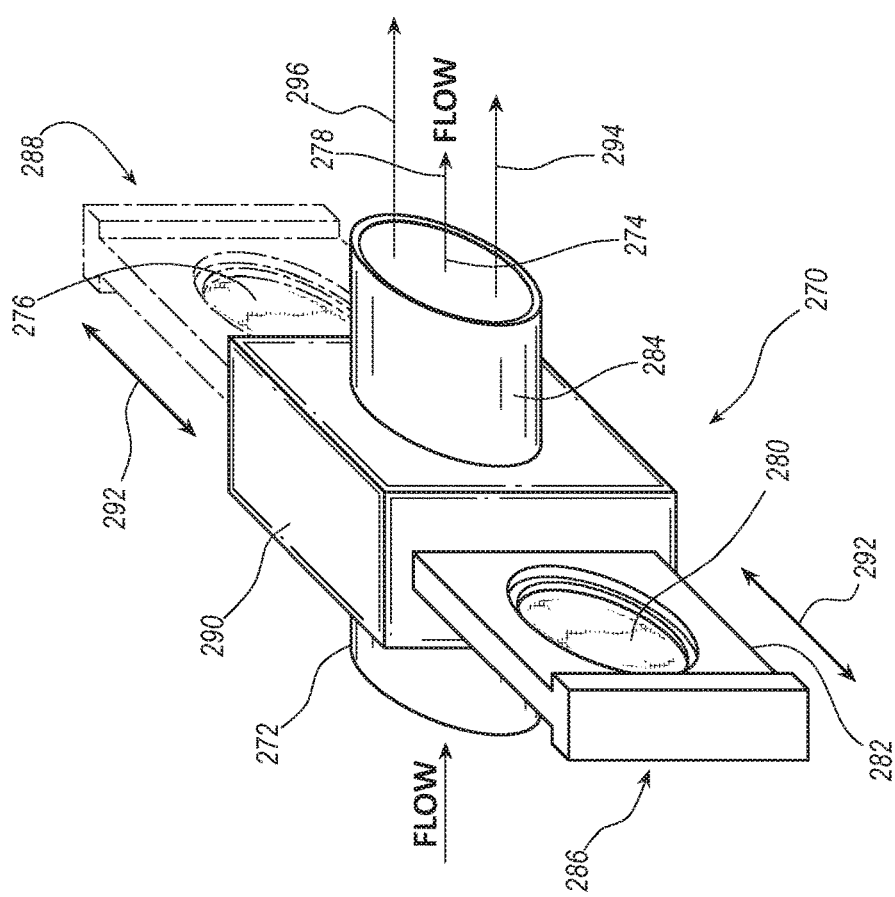
FIG. 9 is a perspective view of a single path dual filter system for use in a pulmonary ventilation system.

FIG. 9 is a perspective view and FIG. 10 is a cross sectional view which illustrate or depict an inline filter arrangement 270 to function as a changeable filter such as changeable filter 62 or changeable inlet filter 450. The inline filter 270 has a first conduit 272 to receive exhaust gas 13 and supply it through a first path 274 through a first filter 276 which removes pathogens from the exhaust gas 13 and supplies first filtered gas 294 at a second conduit 284. The exhaust gas 13 may also be supplied through a second path 278 and a second filter 280 which is also configured to remove pathogens to form filtered second filtered gas 296 for transmission through the second conduit 284. The first conduit 272 and the second conduit 284 are typically force fit with interconnecting hose or lines to receive and transmit gas to and from the filter arrangement 270. Notably, the inline filter 270 may also function as a changeable filter 450 seen in FIG. 2A. That is, blended gas 15 is processed in a fashion through either filter 246 and 248 comparable to exhaust gas 13 to produce breathable gas 11.

As seen in FIGS. 9 and 10, the first filter 276 and the second filter 280 are each mounted to a filter holder 282 that slides relative to the housing 290 between a first position 286 seen in solid in FIG. 9 and second position seen in dotted line 288. In the first position 286, the first filter 276 is in position to receive exhaust gas 13 or blended gas 15 from the first conduit 272 and filter out the pathogens from the exhaust gas to form first filtered gas 294. That is, filter holder 282 positions the first filter 276 in the first path 274 and is movable in the housing 290 to a second position 288 shown in dotted line in FIG. 9. In the second position 288, the first filter 276 is removed from the housing 290 where it may be removed and replaced with a new filter. Alternately, the first filter 276 may be cleaned. In the second position the second filter 280 is positioned in the second path 278 to filter pathogens from the exhaust gas 13 or breathable gas 15 to form second filtered gas 296. The filter holder 282 slides 292 from the second position 288 to the first position 286 so the second filter 280 may be removed and replaced with a new filter or cleaned.

As seen in FIGS. 9 and 10, the first path 274 and the second path 278 are in effect the same but for the filter 276 and 280 through which the exhaust gas 13 or blended gas 15 passes. The filter holder 282 is snuggly fit in the housing 290 and may be sealed with, for example, lubricants or with other mechanical seal material. As seen, the in line filter 270 may be operated between the first position 286 and the second position 288 without venting or releasing to the atmosphere and surrounding areas exhaust gas 13 and blended gas 15 that has not been filtered and in turn contains pathogens. Further, the transition from that first position 286 and the second position 288 can be completed very quickly so there is virtually no noticeable impact on the flow of breathable gas 11 and/or exhaust gas 13 so that the FRC remains unaffected.

Figure 11:
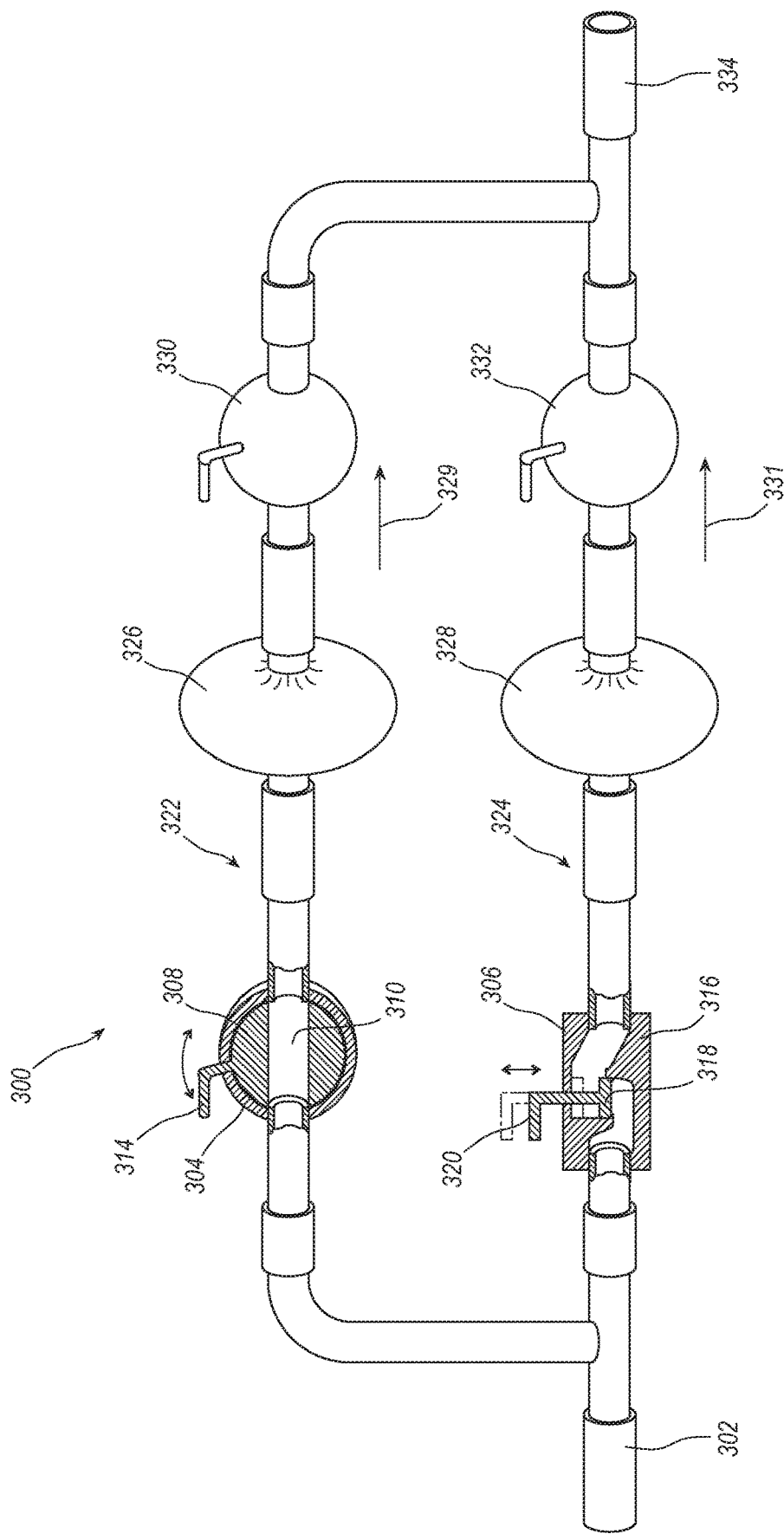
FIG. 11 is a depiction of a dual path changeable filter with partial cross section areas for use in a pulmonary ventilation system.

Referring now to FIG. 11, a changeable filter 300 is shown to be an alternative type of the changeable filter 62 of FIG. 1. The changeable filter 300 has a first conduit 302 to receive exhaust gas 13 from an exhaust line 21 and 44. The exhaust gas 13 and blended gas 15 is directed to either a first valve 304 or a second valve 306. As depicted, the first valve 304 is a ball valve shown in cross section with an interior ball 308 having a channel 310 that can be rotated in a housing 312 between open position in which the channel 310 is aligned to pass exhaust gas 13 therethrough and a second or closed position in which the ball 308 and in turn the channel 310 is rotated by the handle 314 to inhibit movement of exhaust gas 13 therethrough.

The changeable filter 300 as shown to be an alternative type of the changeable inlet filter 450. The changeable filter 300 has a first conduit 302 to receive blended gas 15 from the ventilator output 48. The blended gas 15 is then directed to either a first valve 304 or a second valve 306. As depicted, the first valve 304 is a ball valve shown in cross section with an interior ball 308 having a channel 310 that can be rotated in a housing 312 between open position in which the channel 310 is aligned to pass blended gas therethrough and a second or closed position in which the ball 308 and in turn the channel 310 is rotated by the handle 314 to inhibit movement of blended gas therethrough.

The second valve 306 is a depiction of valve that has a housing 316 with a disc 318 operable by a handle 320 to move the disc between closed (shown) and open positions as known to those skilled in the art. A gate valve may also be used in lieu of either or both first valve 304 and second valve 306. Any other form of valve may be used that functions to stop and permit flow therethrough.

The changeable filter 300 has the first valve 304 in a first leg 322 and the second valve 306 in the second leg 324. The first leg 322 has a first filter 326 configured to filter pathogens from the exhaust gas 13 or blended gas 15 to form first filtered gas 329 that is directed to and through third valve 330 to a discharge 334. Similarly, the second leg 324 has a second filter 328 that functions to filter pathogens from the exhaust gas 13 or blended gas 15 and from second filtered gas 331 that is directed to and through a fourth valve 332 to the discharge 334.

The valves 304, 306, 330 and 332 may be selected to be any one of a ball valve, a gate valve, a disc valve, or other suitable valve as desired by the user. The valves 304, 306, 330 and 332 are operated between open and closed positions for directing exhaust gas 13 or blended gas 15 to and through the first leg 322 and then the second leg 324 in a manner so that no exhaust gas is vented or released to the surrounding area. So for example, valves 304 and 330 are open when valves 306 and 332 are closed. When valves 306 and 332 are closed, the second filter 328 may be removed from the second leg 324 and replaced with a new filter. Upon the connection of a new filter as the second filter 328, valves 306 and 332 may be opened following which valves 304 and 330 are closed. With the valves 304 and 330 closed, the first filter 326 may be removed from the first leg 322 and replaced with a new first filter 326.

Figure 12:
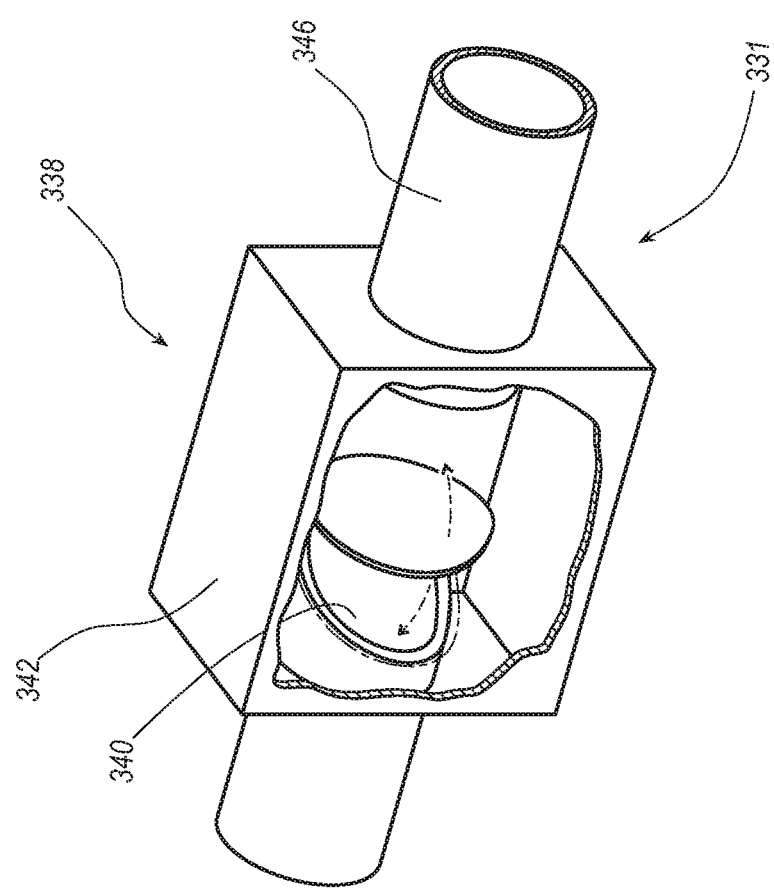
FIG. 12 is a depiction of a check valve useable in the dual path changeable filter of FIG. 11.

In FIG. 12, a check valve 338 is shown which may function as the third and fourth valves 330 and 332. The check valve 338 has a disc 340 that swings between a first position in which the valve disc 340 in the housing 342 is urged into the housing and away from inlet 344 to allow second filtered gas 331 therethrough as depicted in FIG. 12. With second filtered gas 331 entering the housing 342 from the discharge end 346, the valve disc 340 is urged against the inlet 344 to block flow to the first filter 326. The check valve 338 would operate between first and second positions to block flow of the first filtered gas 329 toward the second filter 328 in the same manner. That is, when the valves 304 and 306 are positioned to direct exhaust gas 13 or blended gas 15 through the first leg 322, the valve 330 as a check valve will open and allow filtered exhaust gas to proceed to the valve 332 which would be urged to a closed position by the filtered exhaust gas.

Figure 14:
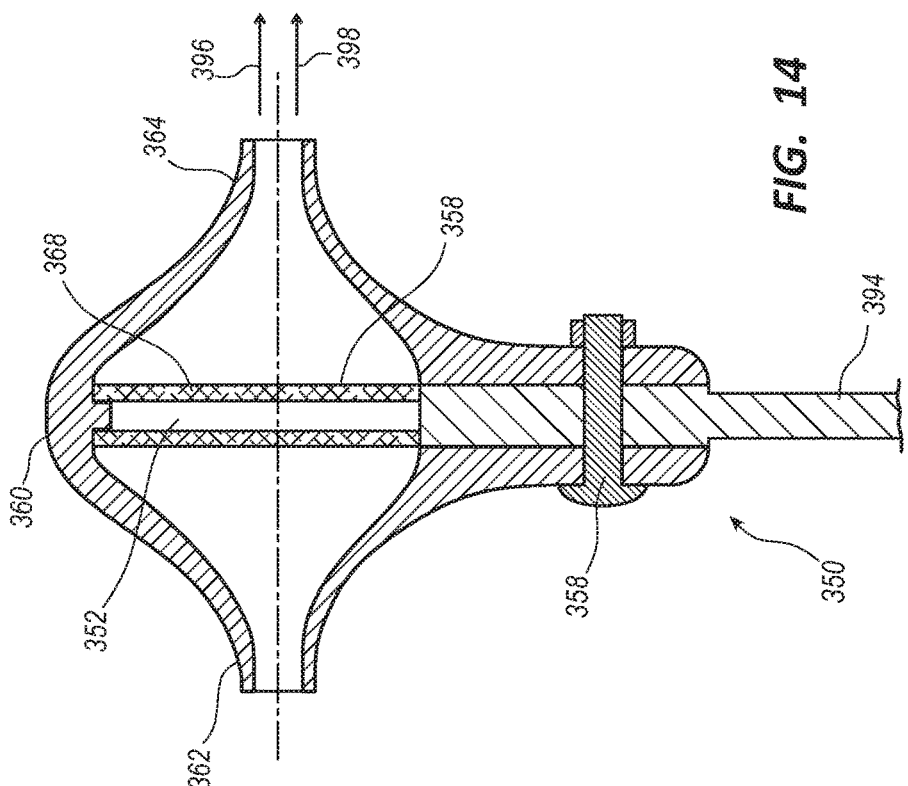
FIG. 14 is a depiction of a partial cross section of the single path dual filter system of FIG. 13.
Figure 13:
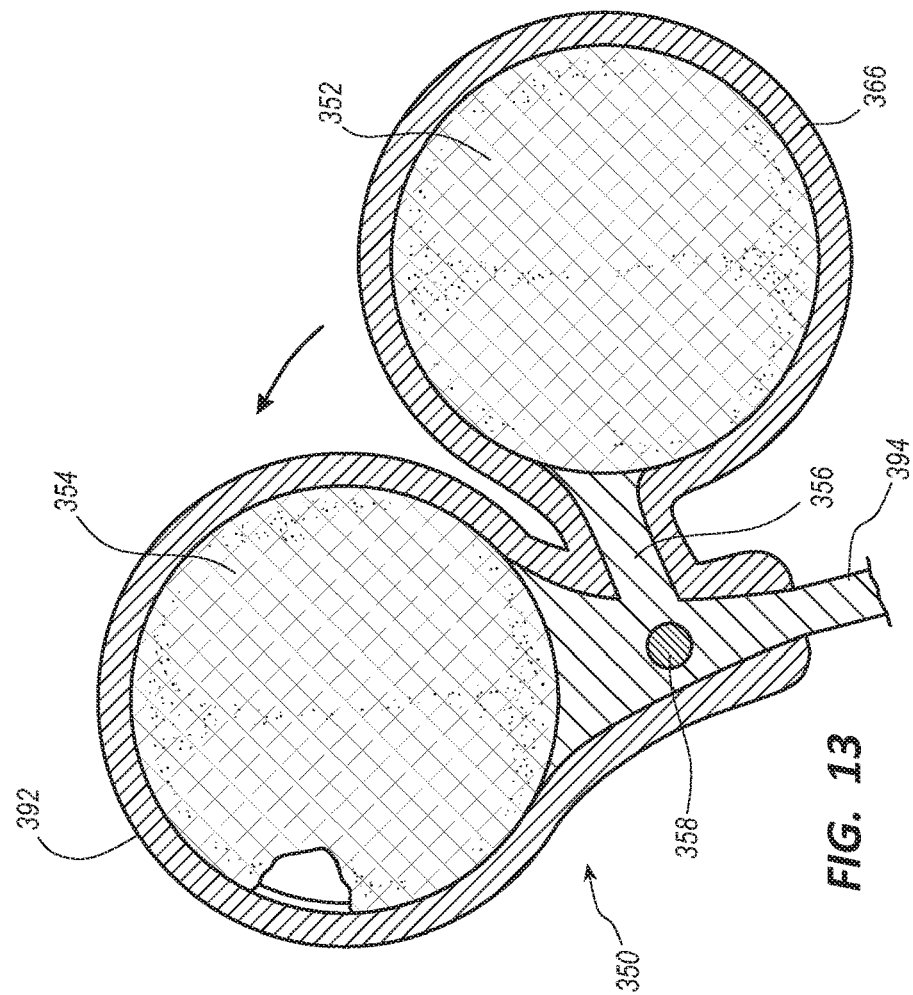
FIG. 13 is a depiction of another single path dual filter system for use in a pulmonary ventilation system.

Referring now to FIGS. 13 and 14, a filter 350 is shown having two filter elements 352 and 354 that are mounted to a holder 356 that rotates about a pin 358. The filter elements 352 and 354 are rotatable about the pin (which can be anything that allows rotation such as a nut and bolt with suitable washers) 358 to move between a first position and a second position. In the first position seen in FIG. 14, filter element 352 is positioned in housing 360 to be in line to filter exhaust gas 13 or blended gas 15 entering the housing 360 from an inlet 362 to remove pathogens there from to create first filtered gas 396 or breathable gas 11 at the outlet 364.

As better seen in FIG. 13, the filter element 352 is circular in projection and secured in first frame 366 which is shown in FIG. 14 to have gaps 368 from the slot 370 only for illustration purposes. The frame 366 is sized to fit snuggly in the slot 370 with optional use of gasket materials such as a strip of felt material to effect an essentially air tight seal.

In FIGS. 13 and 14, the second filter element 354 has a second frame 392 that is joined to or unitarily formed with the first frame 366 and with a handle 394. Then handle 394 can be operated to rotate the first filter element 352 with frame 366 to form its first position in the housing 360 to a second position away from the housing 360 and in turn rotate the second filter element 354 into the housing 360. In turn the first filter element 352 can be cleaned or replaced while the second filter element 354 is functioning to filter the exhaust gas 13 or blended gas 15 to remove pathogens therefrom and form second filtered gas 398. Upon rotation of the second filter element 354 from the housing 360, the first filter element 352 will be reinserted into the housing 360 into its first position. Thus, the second filter element 354 can be cleaned or replaced for use when it is determined that the first filter element is ready to be replaced or cleaned. When the first filter element 352 and the second filter element 354 are rotated in and out of position, the interruption of flow is deemed to be insignificant so that the ventilator will not detect flow problems and automatically take steps to adjust or regulate flow differently to maintain desired flow rate of breathable gas 11.

Figure 15:
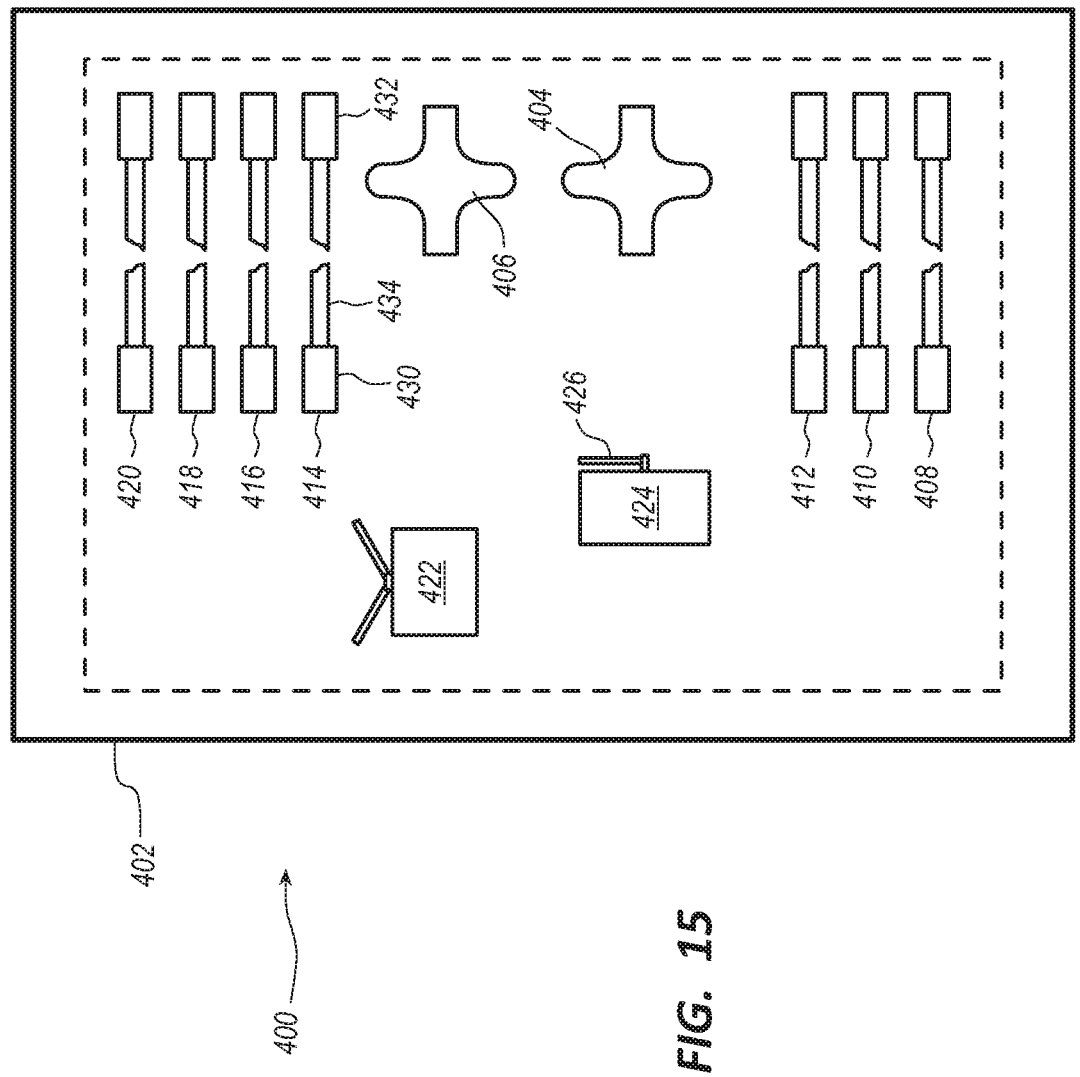
FIG. 15 is a depiction of a kit containing materials to assemble and operate a dual path changeable filter for use in a pulmonary ventilation system.

FIG. 15 depicts a kit 400 having components within a sealed container 402. The container may be a fixed container but also may be a container with flexible sides like a mailing envelope. The components include all those necessary to form a dual path changeable filter of the type disclosed in FIG. 2 or in FIG. 2A. Specifically, the kit 400 contains at least two filters 404 and 406 of the type that can be replaced. Additional filters comparable to filters 404 and 406 can be included or separately packaged. The filters 404 and 406 shown are in line and disposable.

The kit 400 of FIG. 15 also contains conduit or tubing 408, 410, 412, 414, 416, 418 and 420 each sized and sized to effect connections to form a changeable filter system comparable to the one seen in FIG. 2. Additional or fewer tubes may be included depending on the type of changeable filter system to be assembled and operated.

The conduit or tubing 408, 410, 412, 414, 416, 418 and 420 are each configured with suitable connectors 430 and 432 and a suitable stretch 434 in between. The stretch 434 may vary so the user has different sizes available.

The kit 400 also contains a suitable water trap 422 and a suitable diversion valve 424 having a handle 426 operable by the user to move it between a first position and a section position to direct exhaust gas into separate legs each with a filter in it like filters 404 and 406. A separate kit comparable to kit 400 (not shown) may have a humidifier in it and no water trap.

The kit 400 may contain other components including latex or surgical gloves (not shown) for use by operators and sterile wipes (not shown) to maintain suitable cleanliness in the area of operation. Vials or tubes of lubricants for use with the conduit or tubing to effect connections may also be included.

Figure 16:
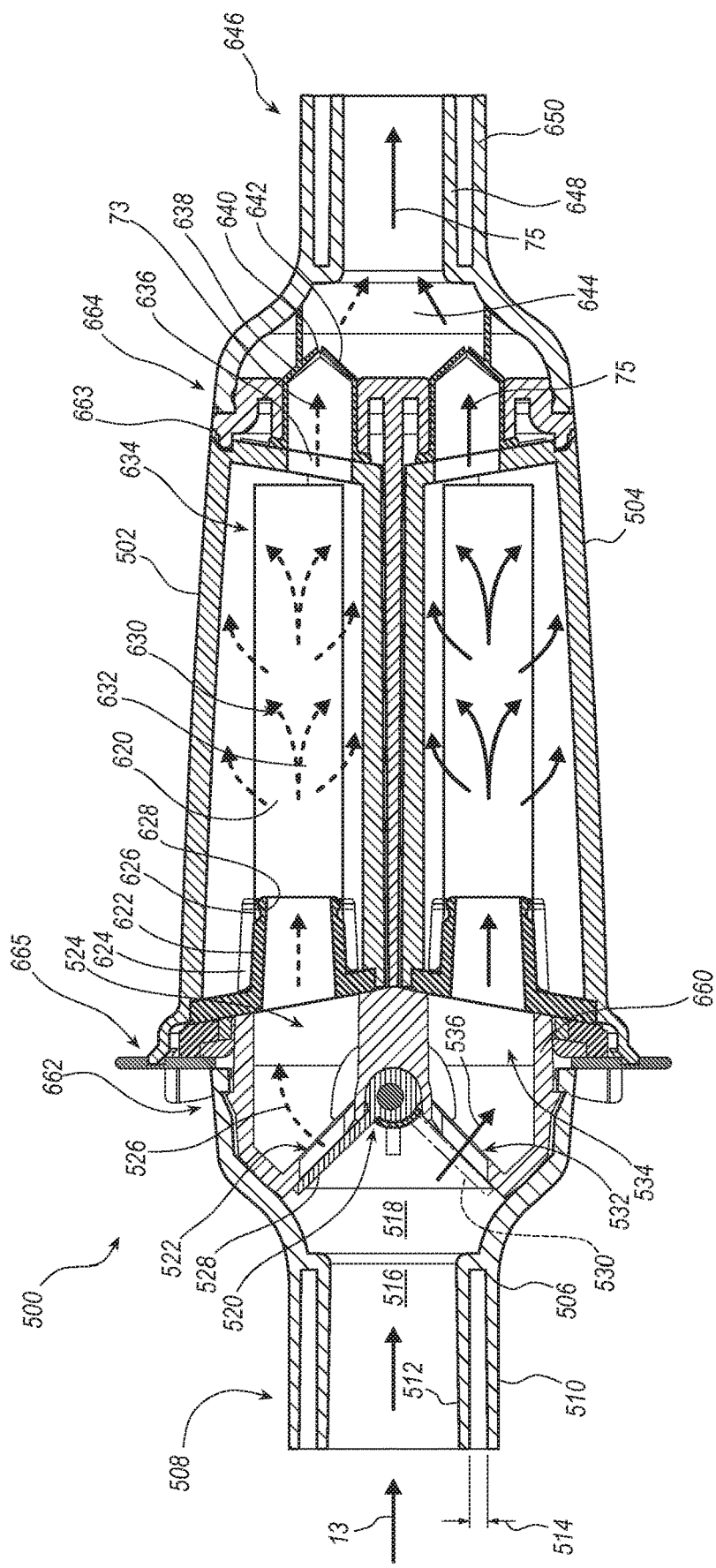
FIG. 16 is a cross section of a dual path changeable filter for use in a pulmonary ventilation system.

Turning now to FIG. 16, a changeable outlet filter 500 is shown in cross section. The outlet filter 500 has a first filter element 502 and a second filter element 504 installed both of which are removable for cleaning and/or replacement as discussed more fully hereinafter. The changeable outlet filter 500 has an input housing 506 having an inlet 508 that has an outer wall 510 that is cylindrical in shape. The inlet has an inner wall 512 spaced from the outer wall 510 a distance 514 to form an opening selected to receive a conduit like conduit 60 (FIG. 2) to effect a secure connection to the changeable outlet filter 500 and to thereby allow the transmission of exhaust gas 13 with pathogens through inlet channel 516. The conduit 60 may be standard 22 millimeter (mm) diameter flexible hose used in medical applications to fit over the outer wall 510 or the standard 15 mm diameter tubing or hose to fit over the inner wall 512. Both walls are tapered and may be said to be conical to meet ISO 5356-1 4th Edition.: 2015. However, different size inlet tubes may be used because the inlet has multiple diameters. Also adapters can be used to accommodate tubing of sizes that are not sized to secure to the inner wall 512 and/or the outer wall 510.

The exhaust gas 13 proceeds through the channel 516 into a valve plenum or chamber 518 which is sized to contain the valve 520 that operates between two positions. In the first position 528 shown, it is blocking the first inlet 522 to prevent the flow of the exhaust gas 13 therethrough into a first path plenum 524 and then into the first filter element 502 as shown by dotted arrow 526. The valve 520 is operable from the first position 528 blocking the first inlet 508 as shown to a second position 530 shown in dotted line blocking second inlet 532. When not blocked, the exhaust gas 13 flows as shown by arrow 536 through the second inlet 532 into a second path plenum 534. With the valve 520 in the second position 530 as shown, the exhaust gas 13 proceeds from the valve plenum 518 through the second inlet 532 into the second path plenum 534 and then into the second filter element 504 as discussed more fully hereinafter.

The valve 520 is shown as a simple face or plate that moves between the two positions 528 and 530 upon operation of a lever not shown in FIG. 16. But the lever not seen for the changeable outlet filter 500 is comparable to the lever 538 seen in a similar changeable outlet filter 540 shown in FIG. 17. That is, the changeable outlet filter 500 and the changeable outlet filter 540 are similar in size shape and function. The outlet changeable filter 540 has a first filter element 542 and a second filter element 544 comparable to the first filter element 502 and the second filter element 504. The lever 538 may be held in place by suitable friction bumps, ball detent systems, or any other arrangement that holds the lever 538 in place but allows the operator to rotate the lever 538 with suitable force applied by the operator's hand.

Figure 18:
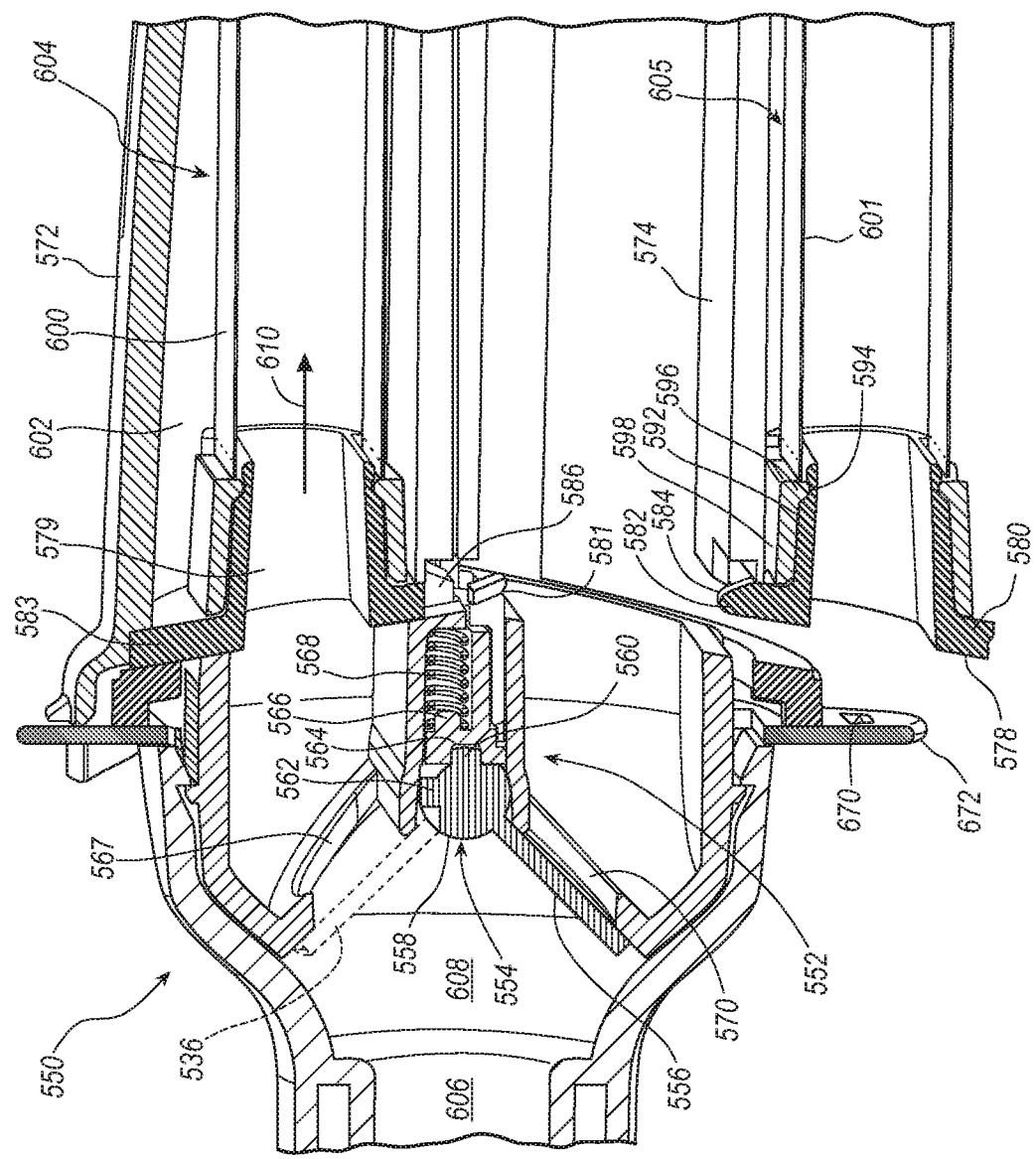
FIG. 18 is an enlarged partial cross sectional view of a changeable outlet filter with a locking mechanism.

FIG. 18 is an enlarged cross sectional view of another changeable outlet filter 550 which is comparable in size, shape and function to the changeable outlet filters 500 and 540. FIG. 18 shows a locking mechanism operable to lock the valve 554 in its second position 556 as shown and in a first position 556 shown in dotted line. The valve shaft 558 has a first finger 560 and a second finger 562 each sized to register with a slot 564 formed in the slide 566. A spring 568 urges the slide 566 to engage the first finger 560 or the second finger 562 into the slot 564 and thereby hold the valve 554 in a closed position blocking the flow of exhaust gas 13 through either the first inlet 567 or the second inlet 570. With its associated inlet blocked, either the associated first filter element 572 or second filter element 574 may be removed for cleaning or replacement while allowing the flow of exhaust gas 13 through the non blocked inlet and preventing the operator from moving the valve 554 to direct the flow of exhaust gas toward the filter element that has been removed. That is, the second inlet 570 is blocked or closed with the second filter element 574 removed for cleaning or replacement.

In FIG. 18, the second filter element 574 has a boss 578 having a base 580 with a rim 582 extending away and in a direction to engage the surface 581 as the second filter element 574 is urged inward toward a secure and operational position comparable to the position of the first filter element 572. As the second filter element 574 moves toward a secure and operational position, the slanted surface 584 of the rim 582 engages and slides on the slanted surface 581 of the slide 566 urging the slide 566 off a finger 560 or 562 so that the valve 554 can be rotated by the operator. When so engaged, the second filter element 574 is in place and ready to function to filter the exhaust gas 13. As so configured, the operator is not able to direct the flow of exhaust gas to a side or path that does not have or contain a filter like filter 502 or 504.

The first filter element 572 also has a boss 579 which is not shown to engage the locking mechanism. In turn it is not here shown to function to operate the slide 566. It is presently believed, that the boss 579 may be formed with a rim 583 comparable to rim 582 with surface comparable to slanted surface 584 to engage another slanted surface (not shown) formed on the extension 586 of the slide 566. In turn, it is believed that the first filter element 572 can be formed to cause the slide 566 to engage and disengage fingers 562 and 564.

As further seen in FIG. 18, the boss 578 has a detent 594 in the cylinder portion 592 configured to snuggly receive a ridge 596 formed in a securing ring 598 to hold the filter media 601 of the second filter element thereto. The first filter element 572 is comparably structured. The filter media 600 of the first filter element 572 has a housing 602 that forms a chamber 604 into which the filter media 600 is located. The exhaust gas 13 (with pathogens) passes through the inlet channel 606 and into the valve plenum 608. The exhaust gas 13 may then pass through inlet 568 or 570 and then through or following a first path or a second path into the interior of the filter media 600 and 601 and then through the filter media into the appropriate chamber 604 or 605. From the chamber 604 or 605, the now filtered exhaust gas passes out of the changeable outlet filter 550 through structure not shown but comparable to that of the changeable outlet filter 500 as more fully discussed hereinafter.

Returning to FIG. 16, the first filter element 502 has a filter media 620 positioned in the chamber 634 while being secured to the boss 622 by a locking ring 624 having a ridge 626 which registers with a detent 628 comparable to that discussed in connection with FIG. 18. The exhaust gas 13 passes 630 into the interior 632 of the filter media 620 and through the filter media 620 into the chamber 634. The exhaust gas 13 thereby becomes filtered exhaust gas 73 that leaves the chamber 634 and proceeds to and through a discharge opening 636 and then through a check valve 638 which is here shown as a duck valve. The check valve 638 has two vanes 640 and 642 that are biased to the closed position as shown. But under pressure from the filtered exhaust gas 73 from the chamber 634, the vanes 640 and 642 open so the filtered exhaust gas 73 may then pass into a discharge plenum 644 and then through an outlet 646 formed in a fashion similar to the inlet 508. That is, the outlet 646 is formed as a socket having an inner wall 648 sized to be connected to a 15 mm medical tube and an outer wall 650 sized to connect to a 22 mm medical tube both in accordance with ISO standard 5356-1 4th Ed.: 2015. The outlet 646 is provided to further transport the filtered exhaust gas 73. In a similar fashion, filtered exhaust gas 75 emanates or exists from the second filter element 504 which is configured comparable to the first filter element 502.

Figure 17:
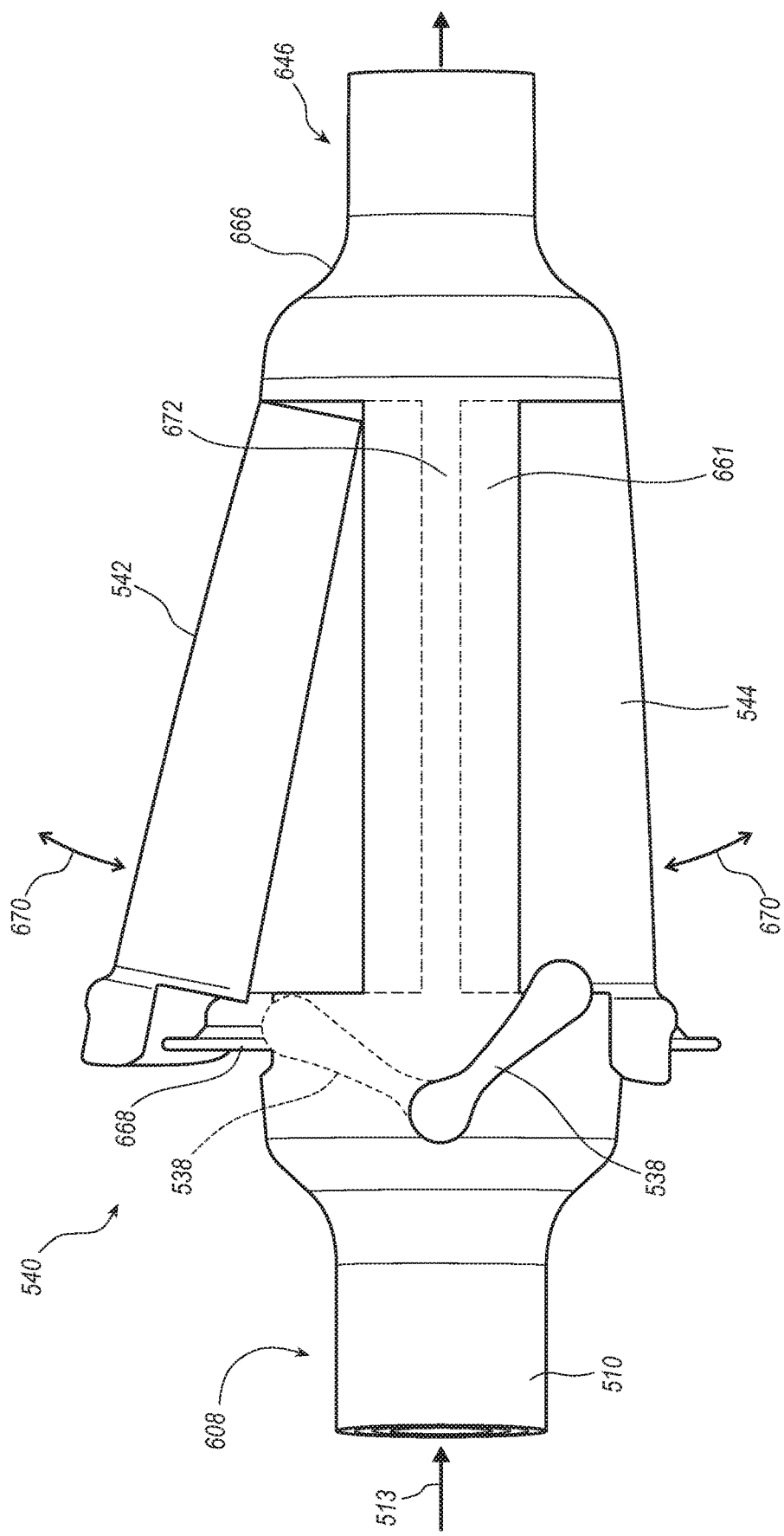
FIG. 17 is a perspective of a changeable outlet filter with a one filter element partially removed.

As seen in FIG. 16, the filter elements 502 and 504 are secured to frame 660; and in FIG. 17, filter elements 542 and 544 are secured to the frame 661 by a mechanical locking structure having a lip and slot 663 at one end and tongue 665 to interact with a groove 557 at the other. The inlet housings 506 in FIGS. 16 and 608 in FIG. 17 are secured by an interlocking ledge structure 662 as best seen in FIG. 16. As also seen in FIG. 16, the outlet 646 is secured by a ridge and detent arrangement 664. Other means may be used for locking the inlet 508 and the outlet 646 so long as they effect stable and effectively air tight closures.

As better seen in FIG. 17, the first filter element 542 is shown removably rotatable 670 relative to the frame 672. That is, the first filter element 542 has a toe at one end (not shown) that engages the frame 672 proximate the outlet 666. A latch (not seen) at the other end engages an opening formed in a wing 668 to lock the first filter element 542 in place. The second filter element 544 is structured comparable to the first filter element 542 so that it has a toe and latch comparable to that of the first filter element 542. The opening in wing 668 is comparable to the opening 670 formed in the wing 672 of the changeable outlet filter 550 seen in FIG. 18. In FIG. 16, an alternate latching arrangement for securing a filter element is shown. The alternate latching arrangement includes the slot and lip 663 at one end of filter element 502 with a groove 557 formed to receive a tongue 665 to provide for removable connection and securement.

Figure 20:
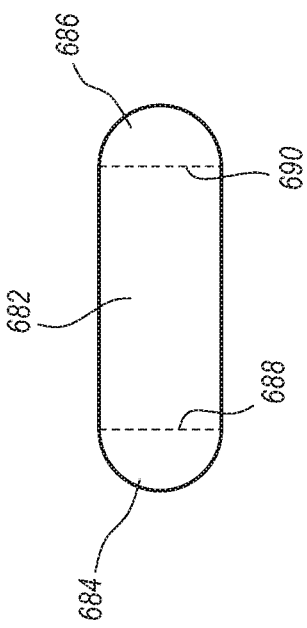
FIG. 20 is a cross sectional view of the filter media of FIG. 19.
Figure 19:
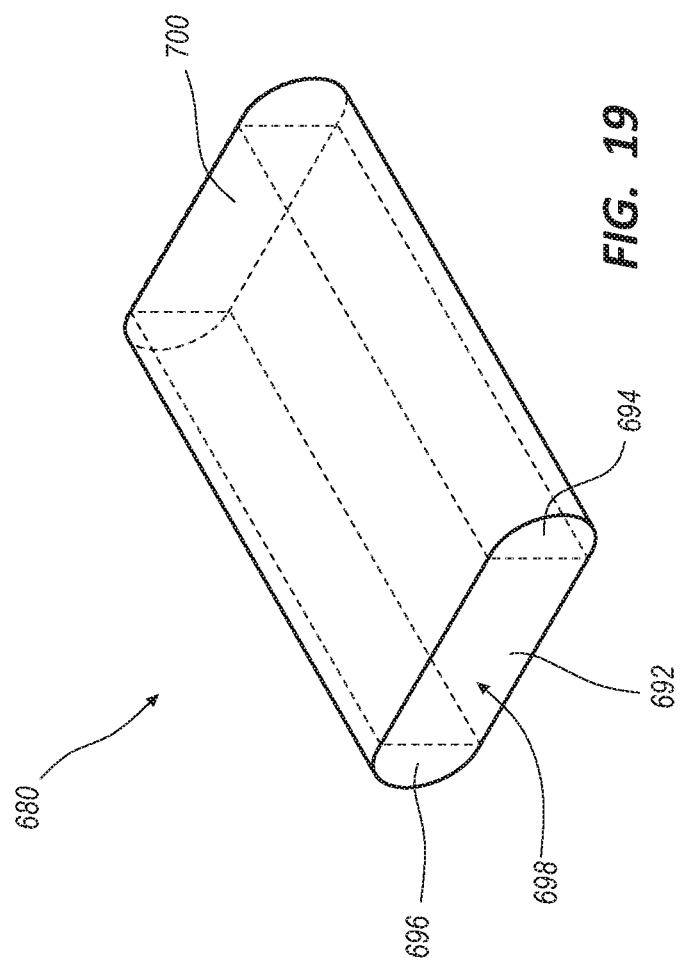
FIG. 19 is a perspective of a filter media for use in a changeable outlet filter.

A filter media 680 is shown in FIGS. 19 and 20. It is formed of a suitable mesh of desired permeability. The material may also be treated with substances to treat any pathogens that may be in the exhaust gas 13. Antiseptic and anti bacterial materials may be used. The filter media 680 is here shown in cross section in FIG. 20 to be a rectangle with two hemispheres 684 and 686 on opposite ends 688 and 690. So in effect, the filter media 680 in cross section is a rectilinear block 692 with a half cylinder 694 and 696 on opposed sides. The front end 698 is open to fit over a boss as hereinbefore discussed. The other end 700 is closed with additional filter material or may be crimped closed.

Figure 21:
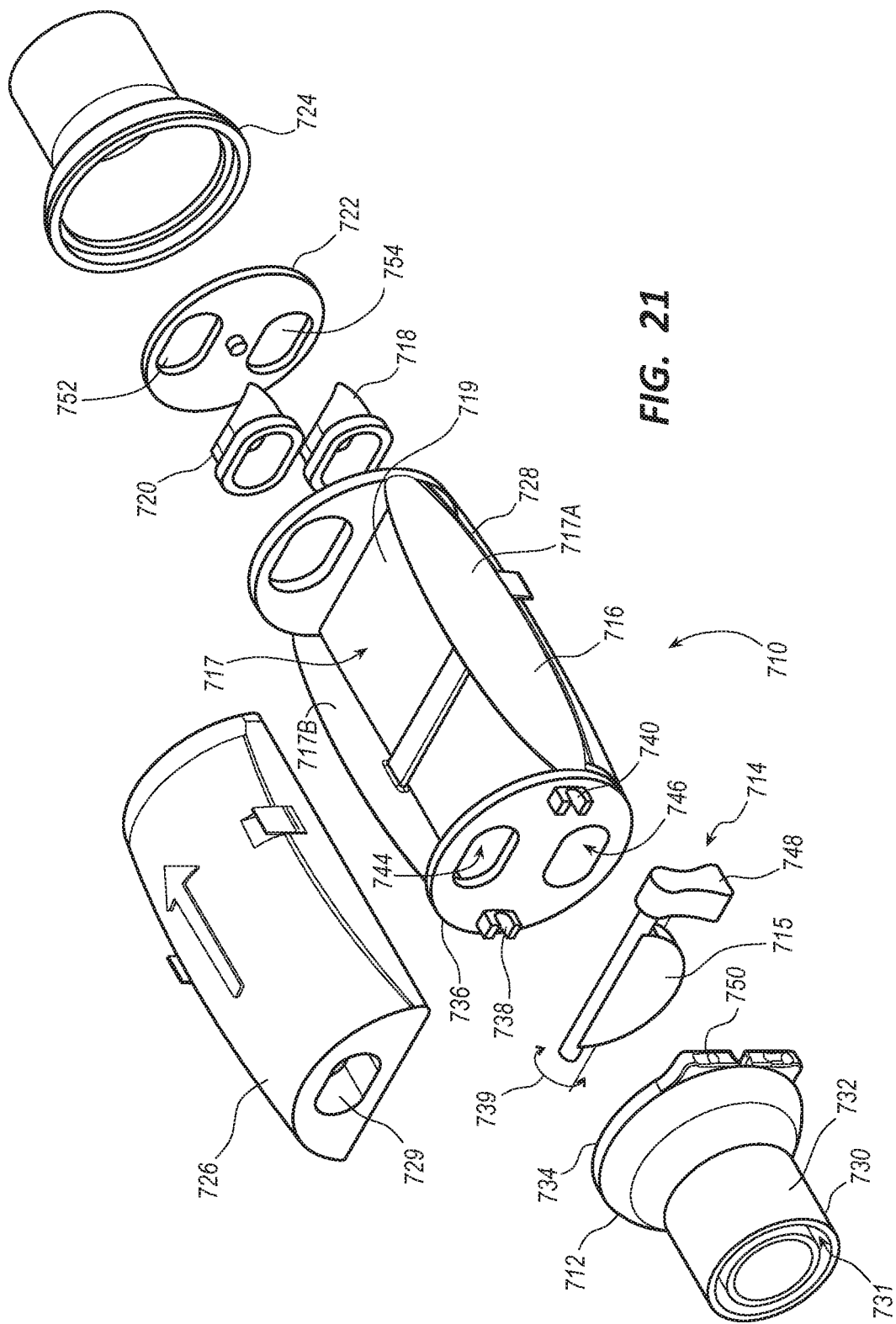
FIG. 21 is an exploded perspective of an alternate changeable outlet filter.

FIG. 21 presents an exploded view of a changeable outlet filter 710 which is similar to the changeable outlet filter 500 of FIG. 16 but simplified in structure. The changeable outlet filter 710 has an inlet 712, a valve 714, a base or frame 716, check vales 718 and 720, valve mount 722, an outlet 724, a first filter element 726 and a second filter element 728. The inlet 712 has an inner wall 730 and outer wall 732 assembled to provide a slot or space there between to receive a medical tube. That is, the slot or space 731 is shaped and sized for secure but removable attachment or connection of a suitable conduit or tube functioning as a conduit. A suitable medical tube may also fit over the outer wall 732.

As seen in FIG. 21, the circular (in projection) rim 734 of the inlet 712 is sized to fit snuggly over the inlet wall 736 of the frame 716. The inlet wall 736 has two snap fit "c" shaped mounting brackets 738 and 740 sized to receive and hold the shaft 742 of the valve 714 but still allow it to rotate 739. The valve 714 is thus free to rotate between a first position to block or close the first inlet aperture 744 and a second position to block or close the second inlet aperture 746. The valve 714 has a handle 748 for operation by the user. The valve handle 748 can be locked in place by detent structure 750 on the rim 734 which registers with a suitable ball structure (not shown) on the bottom of the handle 748. The frame 716 has a void space 717 sized to receive the first filter element 726 with another or second void space separated by a spacer plate 719. The second void space is filled with the second filter element 728. The sides 717A and 717B of the frame 716 are provided to define the void space 717 and provide latching structure to secure the first filter element 726 and second filter element 738 in place. The filter elements 726 and 728 are structured with a boss 729 or similar structure to receive filter material like that seen in FIG. 19. Check valves 718 and 720 are each sized to fit thru suitable openings 752 and 754 in the valve mount 722. The check valves 718 and 720 are shown as duck valves but may be any suitable form of check valve to inhibit back flow and preferably minimize resistance to the flow of filtered exhaust gas therethrough. The outlet 724 is formed similar to the inlet 712 and sized to snuggly receive the valve mount 722 and the outlet wall 732. The outlet 724 is also formed and shaped to connect to an outlet conduit (not shown).

When assembled and connected to operate, the changeable outlet filter 710 receives exhaust gas 13 through the inlet 712. The exhaust gas 13 then passes through one or the other of the inlet openings 744 and 746 which is not blocked by the valve 714 and more particularly by the valve blade 715. After passing through one of the inlet openings 744 and 746, the exhaust gas 13 passes into and through its associated first filter element 726 and second filter element 728. It then passes through the filter media comparable to that shown in FIGS. 19 and 20 and into a void space surrounding the filter media comparable to void spaces 604 and 605 seen in FIG. 18 creating filtered exhaust gas. The filtered exhaust gas then proceeds through one of the valves 720 and 718 and into the outlet 724 for further transmission through the exhaust valve of an associated ventilator.

Figures 22, 23:
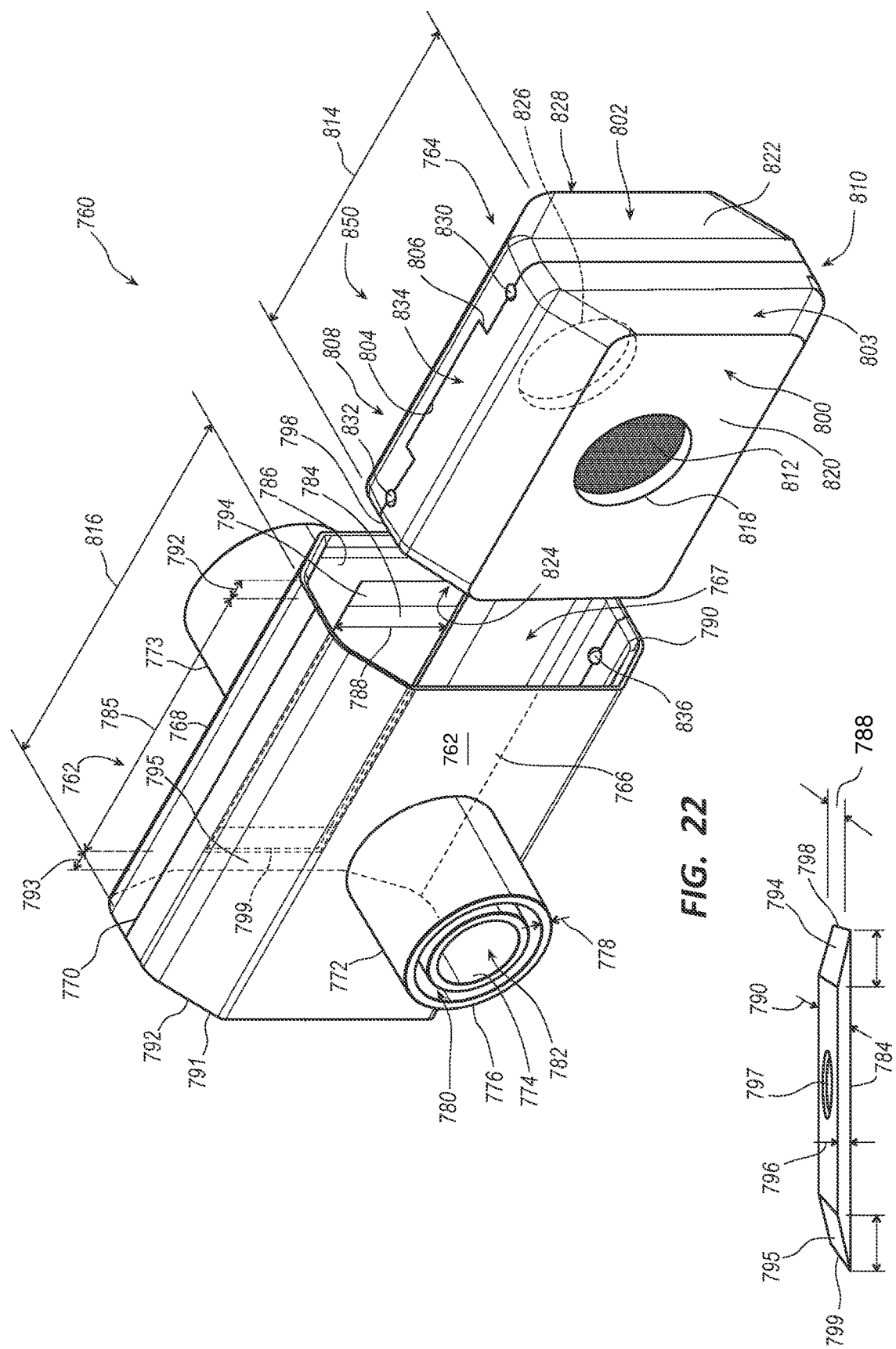
FIG. 22 is a perspective of an alternate changeable outlet filter structure with a housing and cartridge separate.
FIG. 23 is a perspective plane view of seal material for use with the changeable outlet filter of FIG. 22.

FIG. 22 is a perspective and exploded view of a simplified changeable outlet filter 760 having a housing 762 and a changeable first cartridge 764. The housing 762 is formed of two virtually identical halves 766 and 768 assembled together. They may be secured to each other by glue, plastic welding or any other means to effect an air tight and rigid seal along the seam 770. The half 766 has an inlet structure 772 configured to connect to a conduit delivering exhaust gas 13. The inlet structure 772 is formed consistent with the ISO standard hereinbefore mentioned and has an inner wall 774 and an outer wall 776 each of suitable thickness 778. The two walls provide suitable connections for different size hoses. For example a slot or opening 780 sized to receive a conduit which could be, for example, a 15 millimeter diameter medical tube made of a suitable synthetic material. When connected, the tube (not shown) delivers exhaust gas 13 into the channel 782.

The half 766 of the housing 762 has a seal material (not shown for clarity) substantially the same as seal material 784 attached or adhered to the wall 786 on the inside 767 of the other half 768 of the assembled housing 762. The seal material 784 is better seen attached to the wall 786 of the other half 768 and is seen separately in FIG. 23. The seal material 784 as here shown has a height 788 of 0.75 inch and has a width 785 that extends between edges 790 and 791 while being spaced inward from the edges 790 and 791 about ½ inch 792 and 793. As better illustrated in FIG. 23, the seal material 794 has a thickness 796 of about 1/16 of an inch with end portions 794 and 795 formed to taper toward their respective out outer edges 798 and 799 to facilitate the movement of the cartridge 764 into the housing 762.

The seal material 784 in this embodiment is EPDM foam tape but may be other suitable material to form an effective seal between the walls 782 and 786 and the cartridge 764 as more fully discussed hereinafter. Openings 797 are formed in the seal material 785 when installed to register with the channel 782 and a similar channel formed in outlet structure 773.

The changeable cartridge 764 also seen in FIG. 22 is also made of a first half 800 and a second half 802 almost identical to each other. Here, the first half 800 has a tongue 804 on top to register with a groove or inset 806. While a tongue 804 and a inset 806 are shown on the top 808, a comparable tongue and inset structure (not shown) may also be formed in the bottom 810. As seen, the first half 800 and the second half 802 are joined together to form a seam by glue, welding or any other suitable means to join and create an airtight seal between the first half 800 and the second half 802.

When the first half 800 and second half 802 are joined to form the cartridge 764, they form a void space or an interior 803 that is filled with suitable filter material 812. That is, filter material may be layered or sandwiched filter material of the type to filter pathogens and known to those of skill in the art and as discussed hereinafter. The filter material may be flat sheets cut to fit and layered. The filter material may also be pleated to increase the surface area; and the filter material may be formed to function as HME filter material to absorb moisture from exhaust gas leaving the patient and humidify breathable air being inspirated by the patient.

The cartridge 764 has a length 814 that is less than the length 816 of the housing 762 so that when the cartridge 764 is inserted into the interior or inside 767 of the housing 762 with the back wall 822 of the cartridge 764 is not flush with the edge 790. A ledge or lip not shown is then formed to allow another cartridge to be lined up ready to push the first cartridge from its operational location installed in the housing 782. Thus the front wall 824 when installed is set back from the edge 791 of the housing 762 from about ¼ to ¾ of an inch.

When installed in the housing 782, the aperture 818 of the first cartridge formed in the main wall 820 of the first half 800 of the cartridge 764 registers with the channel 782 of the inlet structure 772. At the same time, a second aperture 826 shown in phantom in the other main wall 828 of the second half 802 of the cartridge 764 registers with the second wall aperture formed in the second wall 786 in communication with a channel (not shown) in the outlet 773 comparable to channel 782 in the inlet structure 772. It may be noted that when the cartridge 764 is inserted into the interior or volume 767 of the housing 762, it is secured in place by registering means like a ball and detent arrangement such as balls or bumps 830 and 832 and comparable balls or bumps (not shown) on the side opposite to the top 834 which are positioned to register with corresponding four detents like detent 836 formed in the housing 762.

The changeable outlet filter 760 of FIG. 22 with a cartridge comparable to cartridge 764 may be connected in a pulmonary ventilation system like the system seen in FIG. 2 as the changeable outlet filter 62. That is, the cartridge 764 can be deemed to function as filter 68. When connected, the exhaust gas 13 is introduced via conduit 52 (FIG. 2) into the channel 782 in the inlet 772 (FIG. 22) and then into and through the aperture 771 in wall 786 and the aperture 818 of the cartridge 764 and then into the filter media 812 which functions to filter pathogens out of the exhaust gas 13 to form filtered exhaust gas 73. As stated before, the filter material may be flat sheets of filter material cut to fit and layered. The filter material may also be pleated to increase the surface area; and it may be formed to function as an HME filter material to absorb moisture from exhaust gas leaving the patient and humidify breathable air being inspired by the patient. The filtered exhaust gas 73 proceeds through aperture 826 and aperture 797 through the outlet 783 which is connectable to discharge the filtered exhaust gas 73 to the atmosphere or to the exhaust valve 28.

A second cartridge 850 is then provided comparable or identical in structure and function to cartridge 764. Thus the number 850 is assigned to the same illustration for cartridge 764 to show they are identical. The second cartridge 850 is then pushed or urged toward the interior or volume 767 of the housing 762 in alignment with or to register with the cartridge 764 in place in the housing 762 and to in turn contact rear wall 802 of cartridge 764. By advancing cartridge 850 into the housing 762, one is at the same time advancing the cartridge 764 through and outwardly of the housing 762 with the walls 820 and 828 of the exiting cartridge 764 and then the walls 820 and 828 of the entering cartridge 850 functioning as valve 66 first closing or blocking flow of exhaust gas 13 into the exiting cartridge 764 and then opening as the apertures 818 and 826 come into alignment with the inlet channel 782 in the housing 762 as well as the outlet channel (not shown) in the outlet 783. The cartridge 850 thus functions as filter 70 supplying filtered exhaust gas 75 though the outlet aperture 826 to the outlet channel in the outlet structure 773 and then to atmosphere or to the exhaust valve 28 in the ventilator 10 (FIG. 2). It can be seen that the process of changing the cartridges 764 with cartridge 850 can be completed very quickly. Practically, the change can be effected in a few seconds or less so the ventilation therapy has not effectively been interrupted and the FRC is not affected. Further, exhaust gas 13 has not been released to the surrounding environment. Additional cartridges can be provided so that the change can be completed at whatever interval desired.

Figure 24:
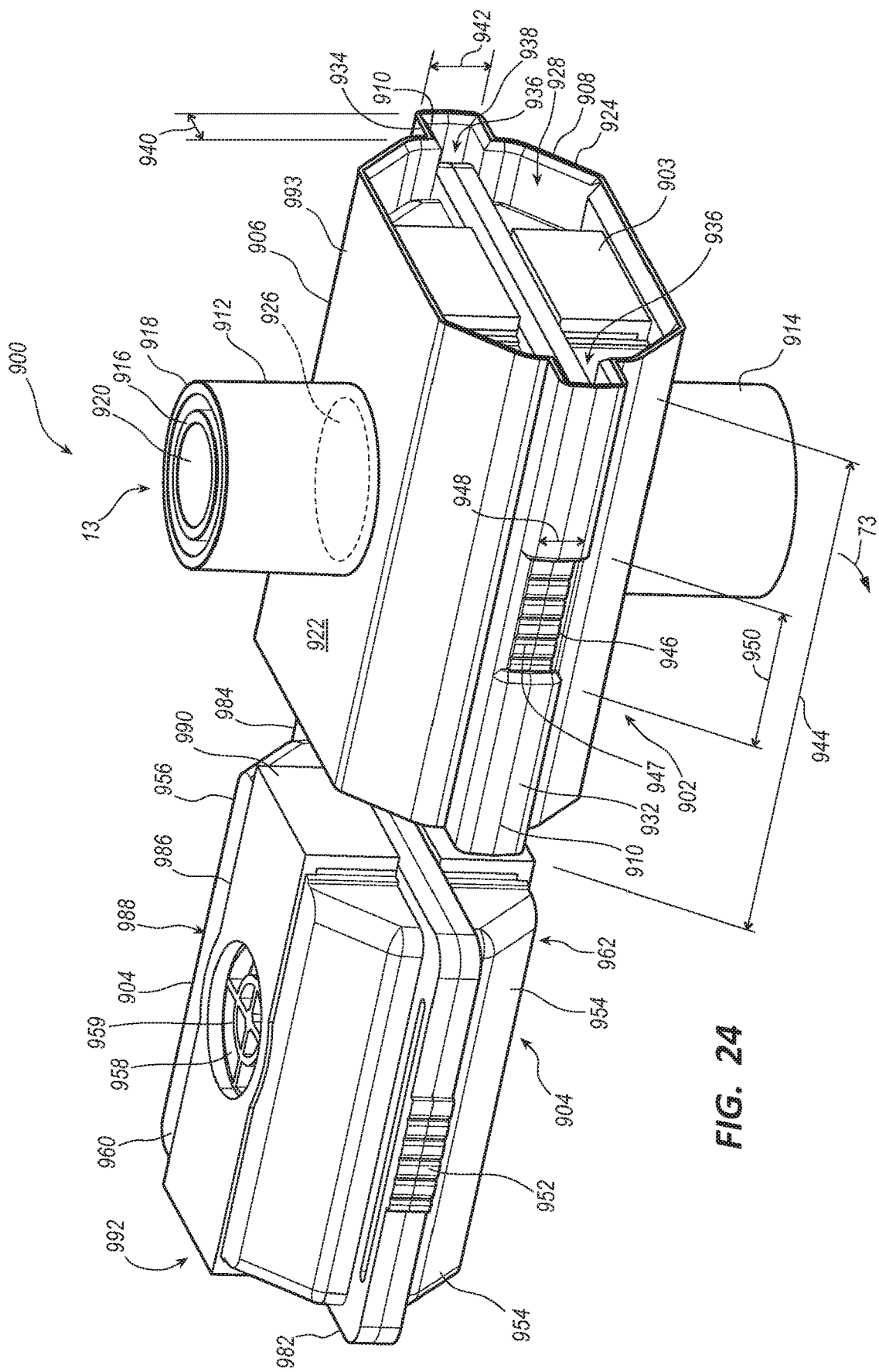
FIG. 24 is a simplified perspective exploded view of a cartridge.

Turning to FIG. 24, a changeable filter structure 900 is shown similar to that of FIG. 22. That is, the filter structure 900 has a housing 902, a first cartridge 903 and second cartridge 904 which is sized and shaped for insertion into the housing 902 in a manner similar to that of the filter shown in FIG. 22. The housing 902 is formed of two identical halves 906 and 908 joined together at seam 910 by glue, welding or any process to fixedly secure the two halves 906 and 908. Alternately, the housing may be formed or molded as one piece.

As shown in FIG. 24, the housing 902 has an inlet 912 and outlet 914. The inlet 902 has an inner wall 916 and an outer wall 918 each having a diameter selected to connect with standard medical tubing as hereinbefore discussed. The inlet 912 is attached to the inlet wall 922 with the channel 920 in alignment with an inlet wall aperture 926 to communicate exhaust gas 13 therethrough into the volume 928 of the housing 902 formed by the two halves 906 and 908.

The outlet 914 is a socket similar to the inlet 912 both having an inner wall (not shown) and an outer wall 930 The inlet 912 and outlet 914 are both formed in accordance with international standards as stated herein to fit with standard 22 mm and 15 mm medical tubing. In addition to the inlet wall 922 and outlet wall 924, the housing 902 has a plurality of sides at its top 932 and its bottom 934 to form the volume or inside 928. As shown, the top 932 has a top slot 936 and the bottom 934 has the bottom slot 938. The bottom slot 938 has a depth 940 and a width 942 and extends the length 944 of the housing 902. The top slot 936 is identical except that it has an opening 946 positioned centrally along the length 944 having a width 948 and a length 950 sized to register with raised portions 952 on the ridge 954 of the cartridge 904 as hereinafter discussed.

The second cartridge 904 seen in FIG. 24 is essentially identical to the first cartridge 903. The second cartridge 904 is formed of two identical halves 954 and 956. The upper half 956 has an inlet aperture 958 formed in the cartridge inlet wall 960. A screen or grid 959. is positioned in the inlet aperture 958 to retain the filter media within the cartridge 904. An outlet aperture (not shown) is identically formed in the outlet wall 962. The first cartridge 903 and the second cartridge 904 each have a plurality of sides to form an enclosed volume that includes the filter media.

Figure 25:
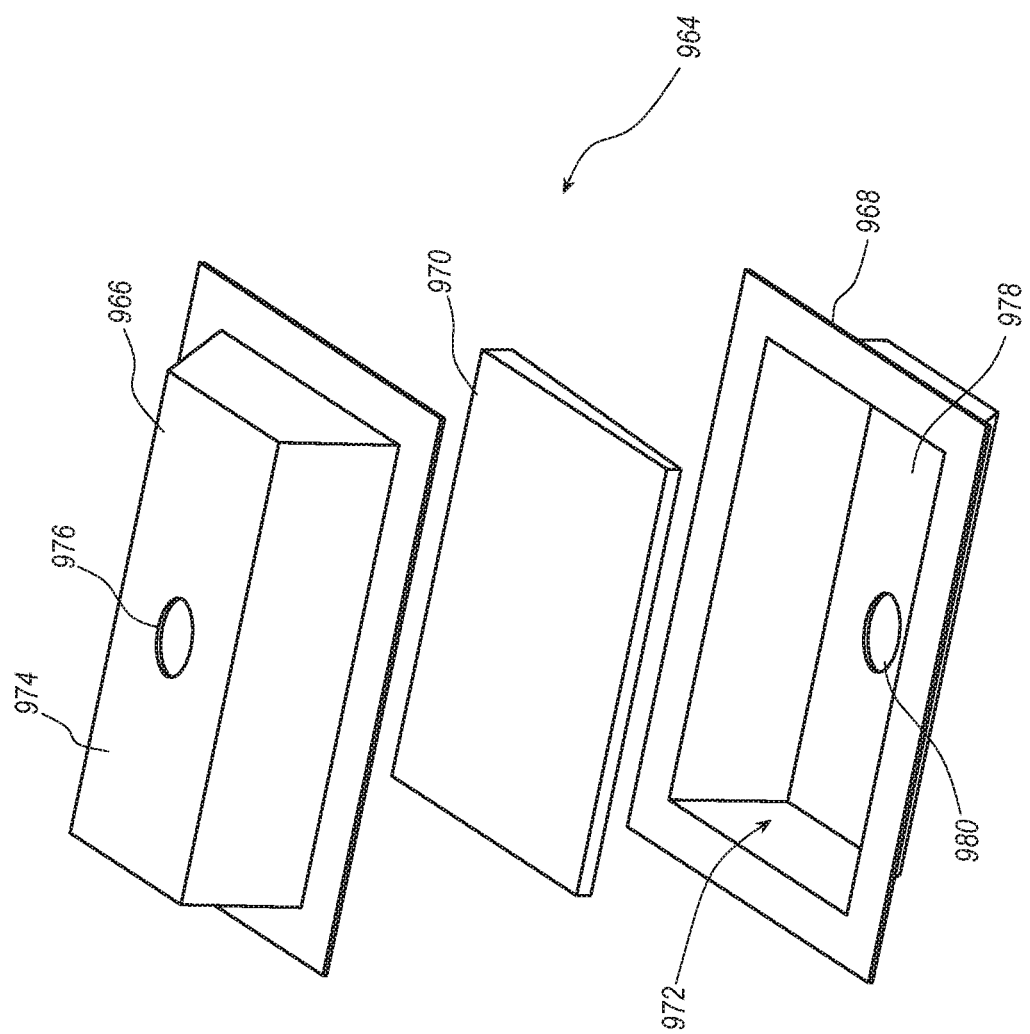
FIG. 25 is a simplified exploded perspective of a cartridge similar to the cartridge of FIG. 24.

As illustrated in a simplified exploded view of a cartridge 964 in FIG. 25, it has a top half 966 and a bottom half 968 with filter media 970 for insertion into the volume 972 formed when the two halves 966 and 968 are joined together. A suitable filter media useful here and for other filter media herein identified is Technostat® 150 Plus available from Superior Felt & Filtration, LLC of McHenry, Ill. The filter material may be several flat sheets cut to fit and layered. The filter material may also be pleated to increase the surface area; and it may be formed to function as an HME filter material to absorb moisture from exhaust gas leaving the patient and humidify breathable air being inspirated by the patient. The top half 966 has an inlet wall 974 with an inlet aperture 976 comparable to inlet aperture 958. The bottom half 968 has an outlet wall 978 having an outlet aperture 980 formed therein.

Returning to FIG. 24, the second cartridge 904 has a top flange or rim 982 and a bottom flange or rim 984 that are sized and shaped to register with the top slot 936 and the bottom slot 938 of the housing 902. A seal material 986 surrounds the cartridge 904 with an inlet aperture 988 in registration with the inlet aperture 958 in the inlet wall 960. The seal material 986 has an outlet aperture in registration with the cartridge outlet wall aperture (similar to the outlet aperture 980 in FIG. 25) and with an outlet aperture (not shown) in the outlet wall of the housing 902. The seal material 986 is placed on the cartridge 904 rather than on the interior of the housing 902. The seal material 986 is elastic and is stretched to fit tightly about the cartridge 904.

Similar to the filter arrangement of FIG. 22, the filter 900 of FIG. 24 has a first cartridge 903 in the housing with the apertures of its inlet wall, outlet wall, and sealing material in alignment forming a first path by which exhaust gas with pathogens like exhaust gas 13 enters channel 920 and proceeds through the cartridge 903 with the pathogens being filtered out to form filtered exhaust gas like exhaust gas 73. When it is desired to remove or replace the first cartridge 903, the second cartridge 904 is presented to the housing 902 with the top ridge 982 and the bottom ridge 984 aligned with top slot 936 and bottom slot 938. Notably, the cartridge 904 is otherwise suitably dimensioned to fit into the volume 928 of the housing 902 and effect a seal between the front face 990 of the second cartridge 904 and the back face of the first cartridge 903 comparable to the back face 992 of the second cartridge 904. The seal material 986 also effects a seal between the inlet wall 922 of the housing 902 and the inlet wall 960 of the second cartridge as well as between the outlet wall 924 of the housing 902 and the bottom 962 of the second cartridge 904. To effect removal of the first cartridge 903, the raised portion 947 formed in its rim extending into the opening 946 in the to slot of the housing is pressed with the fingers to deflect inward as the second cartridge 904 is urged into the volume 928 of the housing 902. That is, rim 982 has a number of raised bumps 952 sized in length and width to register with the opening 946 in the top slot 936 of the housing so the second cartridge is correctly positioned to create the second path when the raised bumps 952 are in registration with the opening 946. In effect the top and bottom walls of the first cartridge and the second cartridge 904 with seal material function as valves closing the first path and opening to form a second path. That is the second path is formed whereby the exhaust gas 13 passes through channel 920 and through inlet wall aperture 926, seal aperture 988, inlet cartridge wall aperture 958 and then into the media within the cartridge 904 to the cartridge wall aperture (like cartridge outlet wall aperture 980 in FIG. 25) and then through an outlet aperture in the seal material 986 to and through the outlet wall aperture of the outlet wall 962 to the channel in the outlet 914 to become filtered exhaust gas comparable to filtered exhaust gas 75.

It should be noted that in some configurations, the first cartridge 903 and the second cartridge 904 of the filter 900 may also have connectors to attach one to the other so that the first cartridge cannot be removed before the second cartridge is properly in place. A train coupling arrangement as hereinbefore discussed is a suitable connector. Other connectors may be used that inhibit detachment of the first cartridge 903 from the second cartridge 904 until the second cartridge 904 is positioned and formed the second path.

Figure 26:
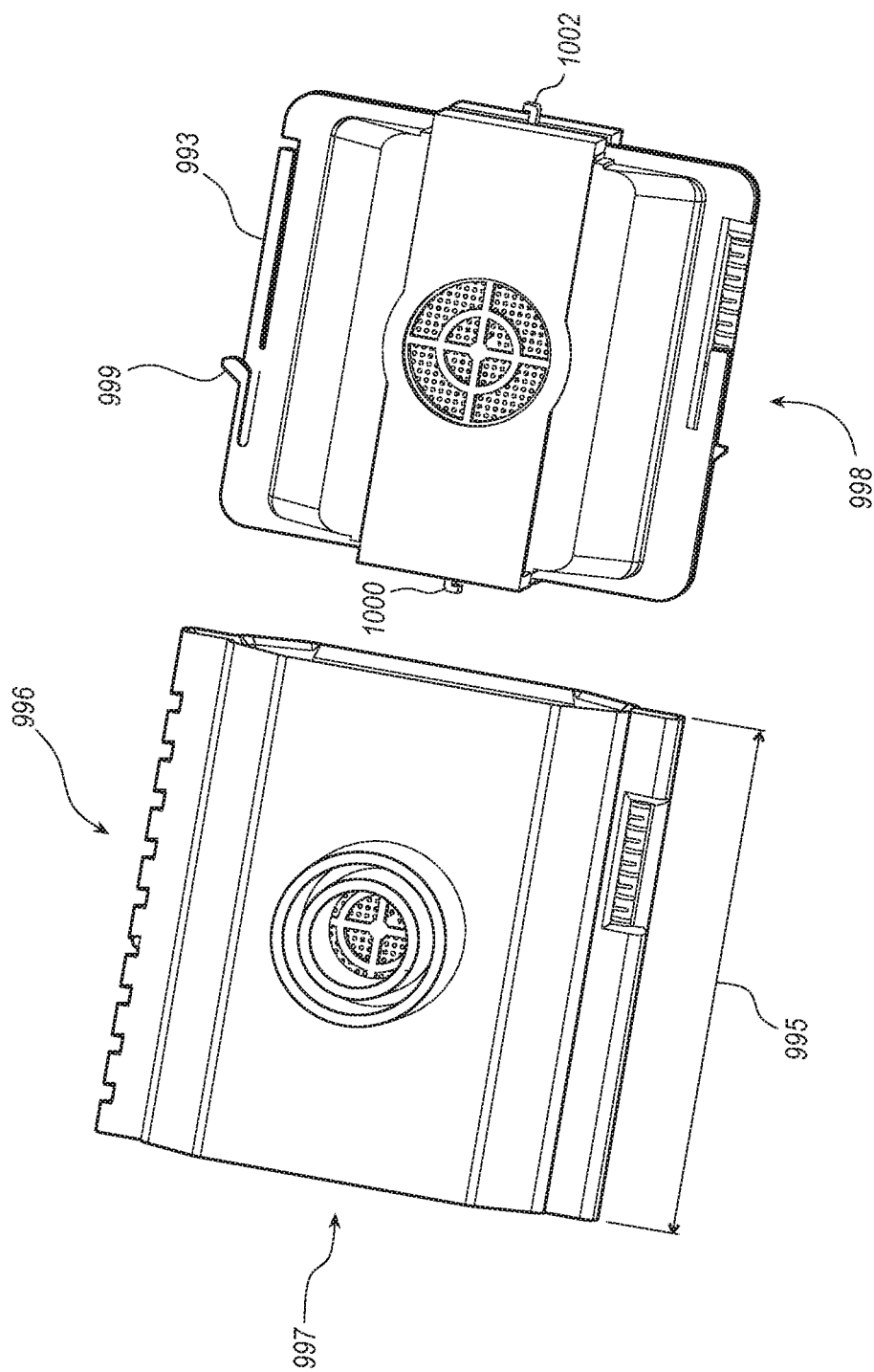
FIG. 26 is a perspective of an alternate changeable outlet filter with a housing and cartridge separated.

In another configuration seen in FIG. 26, a housing 997 similar to housing 902 may be formed with a series of evenly spaced holes 996 along the length 995 of its upper rim as seen in FIG. 26. The first cartridge 998 similar to the second cartridge 904 may be formed to have a flexible pawl 999 positioned on its rim 993 to engage the spaced holes 996 when the second cartridge is inserted into the housing 997 to form a changeable filter structure comparable to changeable filter structure 900. In operation, the pawl 999 can engage the slots 996. The pawl 999 allows the first cartridge 998 to be urged out of the housing 997 by the second cartridge like second cartridge 904 while preventing removal of the first cartridge 998 before insertion of the second cartridge. In short the second cartridge needs to be urged in to push out the first cartridge. Connectors 1000 and 1002 are also depicted on the cartridge 998 to illustrate a coupling arrangement which functions to couple a first cartridge to a second cartridge so that the first cartridge cannot be removed before the second cartridge is in place.

It may be noted that filters herein disclosed may be used as the inlet filter 12 as well as the changeable outlet filter 46. The filter structures particularly illustrated in FIGS. 22, 24 and 25 are particularly suitable for use as the HME filter 17 seen in FIG. 1 with filter media known to those skilled in the art as suitable for HME use. See, for example, HME filter material as disclosed in U.S. Pat. No. 7,594,509 (Burk) at Col3, line 36-54.

Those skilled in the art will recognize disclosed structures and methods may be practiced using materials that may be different from those identified hereinabove without departing from the principles as disclosed. Only specific embodiments have been disclosed to illustrate the structures and methods as defined by the appended claims.

What is claimed is:

1. A pulmonary ventilator system for use with a patient having a trachea, said pulmonary ventilator system being configured to transmit a breathable gas formed of a first gas and a second gas different from said first gas into an input and output device for insertion into said trachea of said patient wherein said breathable gas upon discharge from said patient through said input and output device becomes an exhaust gas with pathogens from said patient, said pulmonary ventilator system comprising:
   a ventilator configured to receive said first gas and said second gas, to blend said first gas and said second gas to form a blended gas, and to supply said blended gas at a ventilator output;
   a first supply line connectable to said ventilator output for receiving said blended gas;
   input filtration structure connected to receive said blended gas from said first supply line, said input filtration structure including an inlet filter to filter said blended gas to form a breathable gas,
   a second supply line connectable to receive said breathable gas from said input filtration and supply said breathable gas through said input and output device to flow into the trachea of said patient;
   an exhaust line having
      a first end connectable to said input and output device for receiving said exhaust gas said pathogens from said patient, and
      a second end spaced from said first end;
   exhaust filtration structure for filtering said pathogens from said exhaust gas to form a filtered exhaust gas, said exhaust filtration structure having an inlet connected to receive said exhaust gas with said pathogens from said second end of said exhaust line, said exhaust filtration structure being configurable to direct said exhaust gas with said pathogens in one of a first path and a second path, said exhaust filtration structure having a first filter removably positionable in said first path to receive said exhaust gas with said pathogens from said inlet to filter said exhaust gas and to form first filtered exhaust gas, and said exhaust filtration structure having a second filter positionable in said second path to receive said exhaust gas with said pathogens from said inlet to filter said exhaust gas with said pathogens to form second filtered exhaust gas;
   a system outlet connected to receive said first filtered exhaust gas and said second filtered exhaust gas to become an outlet gas and to transmit said outlet gas;
   an exhaust valve associated with said ventilator and connected to receive said outlet gas, said exhaust valve being controllable periodically discharge said outlet gas to the atmosphere;
   wherein said exhaust filtration structure has said first filter having,
      a housing that has
         a first wall having a first wall aperture formed therethrough, and
         a second wall spaced from said first wall, said second wall having a second wall aperture formed therethrough,
         said housing having a housing top and a housing bottom assembled with said first wall and said second wall to define a housing volume and said housing having a first open end and a second open end opposite said first open end,
         a housing inlet attached to said first wall and connectable to said second end of said exhaust line, said housing inlet having an inlet channel in registration with said first wall aperture to receive said exhaust gas with said pathogens to form a first portion of said first path, and
         a housing outlet connected to said second wall and having an outlet channel in registration with said second wall aperture,
      a first cartridge
         having a first cartridge wall,
         having a second cartridge wall spaced from said first cartridge wall,
         having a plurality of first cartridge sides, said plurality of first cartridge sides,
         said first cartridge wall and said second cartridge wall all being assembled to define a first cartridge volume,
         said first cartridge being shaped and sized to be positioned in said housing volume through one of said first open end and said second open end of said housing,
         said first cartridge wall having a first cartridge aperture formed therein in to be in registration with said first wall aperture when said first cartridge is positioned in said housing volume,
         said second cartridge wall having a second cartridge aperture formed therein to be in registration with said second wall aperture when said first cartridge is positioned in said housing volume,
         having a first filter media to filter said pathogens in said gas having pathogens, said first filter media being positioned in said first cartridge volume,
         said first cartridge being positionable in said first housing volume to form a second portion of said first path for the transmission of said exhaust gas with said pathogens from said first wall aperture to said first cartridge aperture, through said first filter media, through said second cartridge aperture to said second wall aperture and to said outlet channel, said filtered exhaust gas becoming first outlet gas directed though said outlet to said exhaust valve, and
         first seal means associated with one of said housing and said first cartridge for effecting a seal to inhibit leakage of said exhaust gas with pathogens from said first housing aperture and said first cartridge aperture and to inhibit leakage of said filtered exhaust gas from said second cartridge aperture and said second wall aperture;

said second filter comprising said housing having said inlet channel in registration with said first wall aperture and formed to receive said exhaust gas with said pathogens to form a first portion of said second path and communicate said exhaust gas with said pathogens through said inlet channel and said first wall aperture, a second cartridge having a third cartridge wall having a third cartridge wall aperture formed therein a fourth cartridge wall spaced from said first cartridge wall, said fourth cartridge wall having a fourth cartridge wall aperture formed therein, a plurality of second cartridge sides along with said third cartridge wall and said fourth cartridge wall, all assembled to define a second cartridge volume, said second cartridge being shaped and sized to sealingly slide into said first housing volume through one of said first open end and said second open end of said housing to displace said first cartridge from said housing volume, second filter media to filter said pathogens in said exhaust gas having pathogens, said second filter media being positioned in said second cartridge volume, said second cartridge being positionable in said housing volume between said first wall aperture and said second wall aperture to form a second portion of said first path for the transmission of said exhaust gas with said pathogens from said first wall aperture to said third cartridge wall aperture, through said second filter media and said fourth cartridge wall aperture to form a second filtered exhaust gas directed through said second wall aperture to said second outlet to become second outlet gas directed through said outlet to said exhaust valve; and second seal means associated with one of said housing and said second cartridge for effecting a seal to inhibit leakage of said exhaust gas with pathogens from said first housing aperture and said third cartridge aperture and to inhibit leakage of said second filtered exhaust gas from said fourth cartridge aperture and said second wall aperture.

2. A filter for use in a pulmonary ventilation system having an inlet circuit to supply breathable gas to a patient and an exhaust circuit connected to transmit exhaled gas with pathogens from said patient as exhaust gas with pathogens, said filter comprising:

a housing having a first housing wall with a first wall aperture therein and a second housing wall with a second wall aperture therein, said housing having a plurality of housing sides assembled with said first housing wall and said second housing wall to define a housing volume with a first open end and a second open end opposite said first open end, and said housing having a housing length extending between said first open end and said second open end;

an inlet having an inlet channel formed therein, said inlet being attached to said first housing wall to extend away therefrom and formed to be connectable in said exhaust circuit to receive said exhaust gas with pathogens from said patient and to receive into said inlet channel said exhaust gas with pathogens with said inlet channel aligned with said first wall aperture for the passage of said exhaust gas with pathogens into said first wall aperture;

an outlet having an outlet channel formed therein, said outlet being attached to said second housing wall to extend away therefrom with said outlet channel aligned with said second wall aperture;

a first cartridge having a first cartridge wall, a second cartridge wall spaced apart from said first cartridge wall, and a plurality of first cartridge sides all assembled to define a first cartridge volume, said first cartridge being shaped and sized to slide into one of said first open end and said second open end of said housing;

said first cartridge wall having a first cartridge wall aperture formed therein sized, shaped and positioned to register with said first wall aperture when said first cartridge is positioned in said housing volume;

said second cartridge wall having a second cartridge wall aperture formed therein sized, shaped and positioned to register with said first wall aperture when positioned in said housing volume;

first filter media to filter said pathogens in said exhaust gas having pathogens, said first filter media being positioned in said first cartridge volume;

seal means associated with one of said housing and said first cartridge for effecting a seal to prevent leakage of said exhaust gas with pathogens from between said first wall aperture and said first cartridge wall aperture and between said second wall aperture and said second cartridge wall aperture;

registering means associated with one or both of said housing and said first cartridge for holding said first cartridge in said housing with the first cartridge aperture in registration with said first wall aperture and said second cartridge aperture in registration with said second wall aperture.

3. The filter of claim 2 wherein said housing is formed of two identical halves sealed together.

4. A filter for use in a pulmonary ventilation system for supplying breathable gas to a patient and having an exhaust circuit connected for transmitting exhaled gas with pathogens from said patient as exhaust gas having pathogens, said filter comprising:

a housing having a first housing wall with a first wall aperture therein and a second wall with a second wall aperture therein, said housing having a plurality of housing sides assembled with said first housing wall and said second housing wall to define a housing volume with a first open end and a second open end opposite said first open end;

an inlet having an inlet channel formed therein, said inlet being configured to receive into said inlet channel from said exhaust circuit said exhaust gas having pathogens, said inlet being attached to said first housing wall with said inlet channel aligned with said first aperture for the passage of said exhaust gas having pathogens;

an outlet having an outlet channel formed therein, said outlet being attached to said second housing wall with said outlet channel aligned with said second aperture to be in communication with said housing volume;

a first cartridge having a first cartridge wall, a second cartridge wall spaced from said first cartridge wall, and a plurality of first cartridge sides all assembled to define a first cartridge volume, said first cartridge being shaped and sized to slide into one of said first open end and said second open end of said housing and into said housing volume, said first cartridge wall having a first cartridge aperture formed therein sized and shaped to register with said first wall aperture, said second cartridge wall having a second cartridge aperture formed therein sized and shaped to register with said second wall aperture and a first filter media to filter said pathogens in said exhaust gas having pathogens and positioned in said volume;

registering means associated with one of or both of said housing and said first cartridge for moveably holding said first cartridge in said housing with the first cartridge aperture in registration with said first housing aperture and said second cartridge aperture in registration with said second housing aperture;

a second cartridge having a third cartridge wall, a fourth cartridge wall spaced from said third cartridge wall, and a plurality of second cartridge sides all assembled to define a second cartridge volume, said second cartridge being shaped and sized to slide into one of said first open end and said second open end of said housing to abut and displace said first cartridge, said third cartridge wall having a third cartridge aperture formed therein sized and shaped to register with said first wall aperture, said fourth cartridge wall having a fourth cartridge aperture formed therein sized and shaped to register with said second wall aperture, and a second filter media to filter said pathogens in said exhaust gas having pathogens and positioned in said second cartridge volume;

seal means associated with one of or both of said housing and said first cartridge and said second cartridge for effecting a seal to prevent leakage of said exhaust gas having pathogens from between said first wall aperture and said first cartridge aperture and between said second wall aperture and said second cartridge aperture and for effecting a seal to prevent leakage of said exhaust gas with pathogens from between said first wall aperture and said third cartridge aperture and between said second wall aperture and said fourth housing aperture;

registering means associated with one of and both of said housing and said first cartridge and said second cartridge for moveably holding said first cartridge in said housing with the first cartridge aperture in registration with said first wall aperture and said second cartridge aperture in registration with said second wall aperture and for holding said second cartridge in said housing with the third cartridge aperture in registration with said first wall aperture and said fourth cartridge aperture in registration with said second wall aperture.

5. The filter of claim 4 wherein the length of the first filter cartridge is less than the length of the housing.

6. The filter of claim 4 wherein the plurality of first cartridge sides of the first cartridge includes a first cartridge front and a first cartridge back, and wherein said seal means includes a sealing material that is wrapped around and adhered to the first cartridge wall, the second cartridge wall, the first cartridge front and the first cartridge back and wherein the plurality of second cartridge sides of the second cartridge includes a second cartridge front and a second cartridge back, and wherein said seal means includes a sealing material that is wrapped around and adhered to the third cartridge wall, the fourth cartridge wall, and the second cartridge front and second cartridge back to effect a seal between said second cartridge upon abutting said first cartridge.

7. The filter of claim 4 wherein said housing has a housing top formed in the shape of a housing top slot which extends the length of said housing, wherein said housing has a bottom formed in the shape of a housing bottom slot which extends the length of said housing, wherein said first cartridge has a cartridge top formed in the shape of a first cartridge top ridge sized to register and slide in the housing top slot, wherein said first cartridge has a bottom formed in the shape of a first cartridge bottom ridge to register with and slide in the housing bottom.

8. The filter of claim 4 wherein said first cartridge bottom ridge has a deflectable portion that deflects toward and away from said first wall, said deflectable portion having a raised portion thereon, and wherein said housing bottom slot has an opening to register with said raised portion when said first cartridge is positioned in said housing volume with said first wall aperture in registration with said first cartridge aperture.

9. The filter of claim 4 wherein said first cartridge aperture has a first cartridge grid thereon and wherein said second cartridge aperture has a second cartridge grid thereon.

10. A pulmonary ventilator system for use with a patient having a trachea, said pulmonary ventilator system being configured to transmit a breathable gas formed of a first gas and a second gas different from said first gas into an input and output device for insertion into said trachea of said patient wherein said breathable gas upon discharge from said patient through said input and output device becomes an exhaust gas with pathogens from said patient, said pulmonary ventilator system comprising:

a ventilator configured to receive said first gas and said second gas, to blend said first gas and said second gas to form a blended gas, and to supply said blended gas at a ventilator output;

a first supply line connectable to said ventilator output for receiving said blended gas;

input filtration structure connected to receive said blended gas from said first supply line, said input filtration structure including an inlet filter to filter said blended gas to form a breathable gas, a second supply line connectable to receive said breathable gas from said input filtration and supply said breathable gas through said input and output device to flow into the trachea of said patient;

an exhaust line having
a first end connectable to said input and output device for receiving said exhaust gas with said pathogens from said patient, and
a second end spaced from said first end;

exhaust filtration structure for filtering said pathogens from said exhaust gas to form a filtered exhaust gas, said exhaust filtration structure having an inlet connected to receive said exhaust gas with said pathogens from said second end of said exhaust line, said exhaust filtration structure being configurable to direct said exhaust gas with said pathogens in one of a first path and a second path, said exhaust filtration structure having
a first filter removably positionable in said first path to receive said exhaust gas with said pathogens from said inlet to filter said exhaust gas and to form a first filtered exhaust gas, said first filter having
a housing that has a first wall having a first wall aperture formed therethrough, and a second wall spaced from said first wall, said second wall having a second wall aperture formed therethrough, said housing having a housing top and a housing bottom assembled with said first wall and said second wall to define a housing volume having a first open end and a second open end opposite said first open end, a housing inlet attached to said first wall and connectable to said second end of said exhaust line, said housing inlet having an inlet channel in registration with said first wall aperture to receive said exhaust gas with said pathogens to form a first portion of said first path;

a housing outlet connected to said second wall and having an outlet channel in registration with said second wall aperture;

a first cartridge having a first cartridge wall, having a second cartridge wall spaced from said first cartridge wall, having a plurality of first cartridge sides said first cartridge wall and said second cartridge wall all being assembled to define a first cartridge volume, said first cartridge being shaped and sized to slide into said housing volume through one of said first open end and said second open end of said housing, said first cartridge wall having a first cartridge aperture formed therein in to be in registration with said first wall aperture when said first cartridge is positioned in said housing volume, said second cartridge wall having a second cartridge aperture formed therein to be in registration with said second wall aperture when said first cartridge is positioned in said housing volume, said first cartridge having a first filter media to filter said pathogens in said gas having pathogens and positioned in said first cartridge volume, said first cartridge being positionable in said first housing volume to form a second portion of said first path for the transmission of said exhaust gas with said pathogens from said first wall aperture to said first cartridge aperture, through said first filter media, through said second cartridge aperture to said second wall aperture and to said outlet channel, said filtered exhaust gas becoming first outlet gas directed though said outlet to said exhaust valve; and first seal means associated with one of said housing and said first cartridge for effecting a seal to inhibit leakage of said exhaust gas with pathogens from and between said first housing aperture and said first cartridge aperture and to inhibit leakage of said filtered exhaust gas from and between said second cartridge aperture and said second wall aperture;

and said exhaust filtration structure having a second filter positionable in said second path to receive said exhaust gas with said pathogens from said inlet to filter said exhaust gas with said pathogens to form second filtered exhaust gas;

a system outlet connected to receive said first filtered exhaust gas and said second filtered exhaust gas to become an outlet gas and to transmit said outlet gas;

an exhaust valve associated with said ventilator and connected to receive said outlet gas, said exhaust valve being controllable to periodically discharge said outlet gas to the atmosphere.

11. The pulmonary ventilation system of claim 10 further including registering means associated with one of or both of said housing and said first cartridge for holding said first cartridge in said housing with the first cartridge aperture in registration with said first wall aperture and said second cartridge aperture in registration with said second wall aperture.

12. The pulmonary ventilation system of claim 10 wherein said plurality of first cartridge sides includes a first front and a second front spaced from and opposite said first front, wherein said plurality of second cartridge sides includes a third front and a fourth front spaced from and opposite said third front, wherein said seal means includes a first cartridge seal attached to said first cartridge wall, to said second cartridge wall, to said first front and to said second front, and wherein said seal means further includes a second cartridge seal attached to said third cartridge wall, to said fourth cartridge wall, to said third front and to said fourth front.

13. The pulmonary ventilation system of claim 10 wherein said first filter cartridge has a first cartridge length and said housing has a housing length, and wherein said first cartridge length is less than said housing length.

14. The pulmonary ventilation system of claim 10 wherein said housing has a length and wherein said housing top is formed in the shape of a housing top slot which extends the length of said housing, wherein said housing has a bottom formed in the shape of a housing bottom slot which extends the length of said housing, wherein said first cartridge has a cartridge top formed in the shape of a first cartridge top ridge sized to register and slide in said housing top slot, wherein said first cartridge has a bottom formed in the shape of a first cartridge bottom ridge to register with and slide in said housing bottom slot.

15. The pulmonary ventilation system of claim 14 wherein said housing top slot has a plurality of notches formed through and along said length of said housing to form a ratchet structure; and wherein the first cartridge ridge has a pawl oriented at an angle to engage each of said plurality of notches when said first cartridge is being urged into said housing volume.

16. The pulmonary ventilation system of claim 14 wherein said first cartridge bottom ridge has an arm portion that deflects toward and away from said first wall, said arm portion having a raised portion thereon, and wherein said housing bottom slot has an opening to register with said raised portion when said first cartridge is positioned in said housing volume and said first wall aperture is in registration with said first cartridge aperture.

17. The pulmonary ventilation system of claim 12 wherein said first cartridge aperture has a first cartridge grid thereon and wherein said second cartridge aperture has a second cartridge grid thereon.

18. The pulmonary ventilation system of claim 10 further including a coupling having a first connector and a second connector that interact to removably connect one to the other but when connected inhibit separation of said first connector and said second connector and wherein said first cartridge has a first connector of said coupling attached to one of said first front and said second front of said first cartridge, and wherein said second connecter of said coupling is attached to one of said third front and said fourth front of said second cartridge for connecting to said first connector to inhibit movement of said first cartridge relative to said second cartridge.

19. The filter of claim 10 wherein said housing top slot has a plurality of notches with openings formed therein along the length of said housing slot to be a ratchet;

where the first cartridge ridge has a pawl along said cartridge slot positioned to engage each notch when being urged into said housing volume.

\* \* \* \* \*